United States Patent [19]

Suzuki et al.

[11] Patent Number: 4,971,964
[45] Date of Patent: Nov. 20, 1990

[54] PYRIDINE DERIVATIVES

[75] Inventors: Koji Suzuki, New Haven, Conn.;
Hiroyuki Obase, Shizuoka, Japan;
Akira Karasawa, Shizuoka, Japan;
Shiro Shirakura, Shizuoka, Japan;
Kazuhiro Kubo, Shizuoka, Japan;
Ichiro Miki, Shizuoka, Japan; Akio
Ishii, Shizuoka, Japan

[73] Assignee: Kyowa Hakko Kogyo Co., Ltd., Tokyo, Japan

[21] Appl. No.: 366,527

[22] Filed: Jun. 15, 1989

[30] Foreign Application Priority Data

Jun. 20, 1988 [JP] Japan .................. 63-151678

[51] Int. Cl.$^5$ .................. A61K 31/55; C06D 471/04
[52] U.S. Cl. .................. 514/215; 514/278;
514/290; 540/221; 540/543; 540/577; 546/17;
546/65; 546/93
[58] Field of Search .................. 546/17, 65, 93;
540/521, 543; 340/577; 514/215, 278, 290

[56] References Cited

U.S. PATENT DOCUMENTS 3,366,635 6/1968 Villani .................. 346/93
3,633,989 1/1972 Van Der Steldt et al. .......... 546/93

FOREIGN PATENT DOCUMENTS 78584 12/1920 German Democratic Rep. .................. 540/577

Primary Examiner—Robert T. Bond
Attorney, Agent, or Firm—Nixon & Vanderhye

[57] ABSTRACT

A pyridine derivative represented by formula (I):

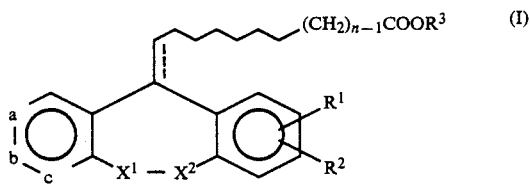

wherein the symbols are as defined in the specification, which exhibits selective, potential, and long-lasting inhibitory activity on biosynthesis of thromboxane $A_2$ and is useful in the treatment and prevention of a broad range of diseases.

9 Claims, No Drawings

PYRIDINE DERIVATIVES

FIELD OF THE INVENTION

This invention relates to novel pyridine derivatives which specifically inhibit the biosynthesis of thromboxane A2 (hereinafter abbreviated as TXA2) and are useful as therapeutic agents or preventive agents in the treatment of a broad range of diseases.

BACKGROUND OF THE INVENTION

It is known that TXA2 is a powerful platelet aggregating agent and also a strong vasoconstrictor as described in Shozo Yamamoto (ed.), *Arachidonate Cascade and Drugs*, Gendai Iryosha (1985). TXA2 also acts as a strong constrictor of the bronchi and tracheal smooth muscle. TXA2 is thus considered to be involved in a broad range of diseases as enumerated below.

(1) Ishaemic diseases, e.g., myocardial infarction, angina pectoris, and thrombosis (2) Cerebral vascular diseases, e.g., temporary ischemia, migraine, apoplectic stroke, and infarct (3) Peripheral vascular diseases and diseases caused by lipid imbalance, e.g., atherosclerosis, capillary vasospasm, peripheral circulatory insufficiency, hypertension, and pulmonary embolism (4) Inflammatory and allergic diseases, e.g., bronchial asthma, bronchitis, pneumonia, naphritis, and hepatitis (5) Shocks, and (6) Metastasis of cancers It is therefore expected that a compound inhibiting TXA2 synthase would have therapeutic effects in the treatment or prevention of one or more of the above-described diseases or any other diseases on which inhibition of TXA2 synthase exerts a favorable influence. Further, when combined with conventional medicines whose usefulness has been limited due to appearance of side effects involving or probably involving TXA2, such a compound is expected to reduce the side effects.

Typical examples of the conventional inhibitors of TXA2 biosynthesis are recited in *Yuki Gosei Kagaku Kyokaishi*, Vol. 45, p. 2 (1987). Further included in the TXA2 biosynthesis inhibitors are imidazole derivatives of formula:

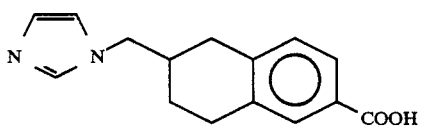

as disclosed in JP-A No. 61-18770 (the term "JP-A" as used herein means an "unexamined published Japanese patent application") corresponding to U.S. Pat. Nos. 4,665,188 and 4,777,257 and pyridine derivatives of formula:

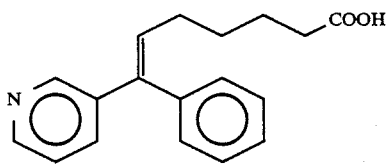

as disclosed in JP-A No. 60-100555 corresponding to U.S. Pat. No. 4,563,446 both of which carry a carboxyl group at the terminal.

Tricyclic pyridine derivatives relevant to the compounds according to the present invention include benzocycloheptapyridine derivatives having formula (II) hereinafter described wherein X¹—X² is —CH=CH— or —CH₂CH₂—, and those wherein the oxo (=O) is replaced by an imino group (=NR) or an amino group (—NHR) as described in *J. Heterocyclic Chem.*, Vol. 19, p.897 (1982) and ibid, Vol. 19, p.967 (1982); and benzocycloheptapyridine derivatives of formula (II) wherein X¹—X² is

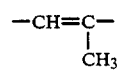

and the oxo is replaced by a methyl group and a hydroxy group or an acetamido group as described in *J. Heterocyclic Chem.*, Vol. 23, p. 961 (1986).

SUMMARY OF THE INVENTION

An object of this invention is to provide a novel and useful TXA2 synthase inhibitor, which is expected to exhibit therapeutic and preventive effects on a broad range of disease.

This invention relates to a pyridine derivative represented by formula (I):

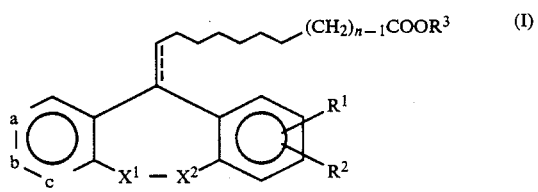

wherein ≡≡≡ represents a single bond or a double bond; R¹ and R², which may be the same or different, each represents a hydrogen atom, a lower alkyl group, a hydroxy group, a lower alkoxy group, a lower alkylthio group, or a halogen atom, or they are taken together to form a methylenedioxy group; R³ represents a hydrogen atom or a lower alkyl group; n represents an integer of from 1 to 10; X¹—X² represents

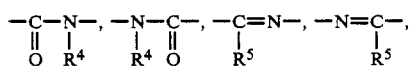

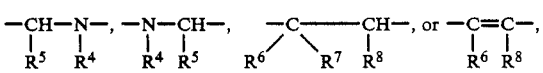

wherein R⁴ represents a hydrogen atom, a lower alkyl group, or a substituted or unsubstituted aralkyl group; R⁵ represents a hydrogen atom, a lower alkoxy group, or a lower alkylthio group; and R⁶ and R⁸, which may be the same or different, each represents a hydrogen atom, a lower alkyl group, or a lower alkenyl group; R⁷ represents a hydrogen atom; or R⁶ and R⁷ are taken together to form

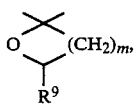

wherein R[9] represents a lower alkyl group; and m represents an integer of from 1 to 3; and any one of a, b, and c represents a nitrogen atom or an N-oxide (N→O), with the other two representing a carbon atom, [hereinafter referred to as compound (I) ] or a pharmacologically acceptable salt thereof.

This invention further relates to a pyridine derivative which is a useful intermediate for synthesizing the compound (I), said pyridine derivative being represented by formula (II)':

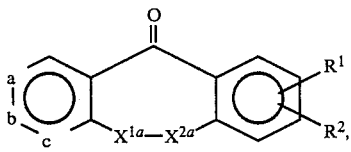

(II)

wherein R[1], R[2], a, b and c are as defined above; and X[1a]—X[2a] represents

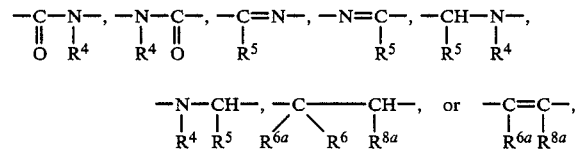

wherein R[4], R[5], and R[7] are as defined above; R[6a] and R[8a], which may be the same or different, each represents a hydrogen atom, a lower alkyl group, or a lower alkenyl group, provided that they do not simultaneously represent a hydrogen atom; or R[6a] and R[7] are taken together to form

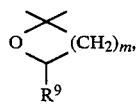

wherein R[9] and m are as defined above.

DETAILED DESCRIPTION OF THE INVENTION

In formulae (I) and (II)', the term "alkyl" in "lower alkyl, lower alkoxy or lower alkylthio group" includes a straight chain or branched alkyl groups having from 1 to 6 carbon atoms, e.g., methyl, ethyl, n-propyl, isopropyl, n-butyl, isobutyl, s-butyl, t-butyl, n-pentyl, isopentyl, and n-hexyl groups. The term "halogen" includes fluorine, chlorine, bromine, and iodine atoms. The term "lower alkenyl" includes alkenyl groups having from 2 to 6 carbon atoms, e.g., vinyl, allyl, propenyl, butenyl, pentenyl, and hexenyl groups. The term "substituted or unsubstituted aralkyl" in the definition of R[4] includes benzyl, phenethyl, and benzhydryl groups which may have 1 to 3 substituents, which may be the same or different, e.g., a lower alkyl group, a lower alkoxy group, a lower alkenyl group, a trifluoromethyl group, a halogen atom, and a methylenedioxy group. In these substituents, the terms "lower alkyl", "lower alkoxy", "lower alkenyl", and "halogen" are as defined above.

In formula (I), one of R[1] and R[2] is preferably a hydrogen atom, a $C_{1-4}$ alkyl group, a $C_{1-4}$ alkoxy group, a halogen atom and the other is a hydrogen atom. n is preferably an integer of from 1 to 7. X[1]—X[2] is preferably

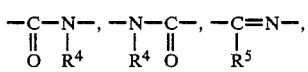

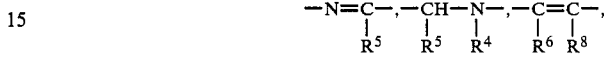

wherein R[4], R[5], R[6] and R[8] are as defined above. A preferable combination of a, b and c is nitrogen, carbon and carbon or carbon, nitrogen and carbon, respectively.

In formula (II)', the preferred embodiments of X[1a]—X[2a] is the same as X[1]—X[2] of formula (I) as mentioned above. R[1], R[2], a, b and c are preferably those as mentioned in formula (I) above.

The pharmacologically acceptable salts of the compound (I) include acid addition salts, metal salts, ammonium salts, organic amine addition salts, and amino acid addition salts. Examples of the acid addition salts are inorganic acid salts, e.g., hydrochloride, sulfate, and phosphate; and organic acid salts, e.g., acetate, maleate, fumarate, tartarate, and citrate. Examples of the metal salts are alkali metal salts, e.g., sodium salt and potassium salt, alkaline earth metal salts, e.g., magnesium salt and calcium salt, aluminum salt, and zinc salt. The ammonium salts include salts with ammonium or tetramethylammonium. The organic amine addition salts include addition salts with morpholine piperidine, etc. The amino acid addition salts include salts with lysine, glycine, phenylalanine, etc.

The compound (I) can be prepared from a compound represented by formula (II):

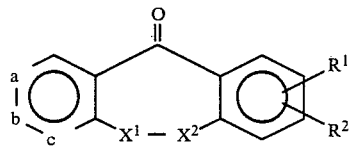

(II)

wherein X[1]—X[2], R[1], R[2], a, b, and c are as defined above.

Synthesis of the compound of formula (II) is illustrated below, but is not limited thereto.

Process 1-1

Preparation of Compound (IIa)

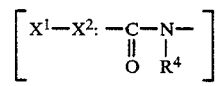

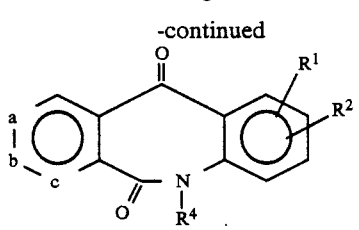

wherein $R^1$, $R^2$, $R^4$, a, b, and c are as defined above.

The compound (IIa) can be synthesized according to the following reaction scheme:

In the definition of A, the metal referred to means an alkali metal, e.g., lithium, sodium and potassium, and the carboxylic acid equivalent includes —$CONR^{10}R^{11}$ (wherein $R^{10}$ and $R^{11}$, which may be the same or different, each represents a hydrogen atom or a lower alkyl group) or a residue of an oxazoline derivative, e.g., 4,4-dimethyloxazoline. The lower alkyl group in the definition of $R^{10}$ or $R^{11}$ is as defined above.

According to the above reaction scheme, the compound (1) is reacted with 1 to 2 equivalents of an alkyl metal, e.g., lithium diisopropylamide, in an inert solvent such as ethers (e.g., diethyl ether, tetrahydrofuran) at

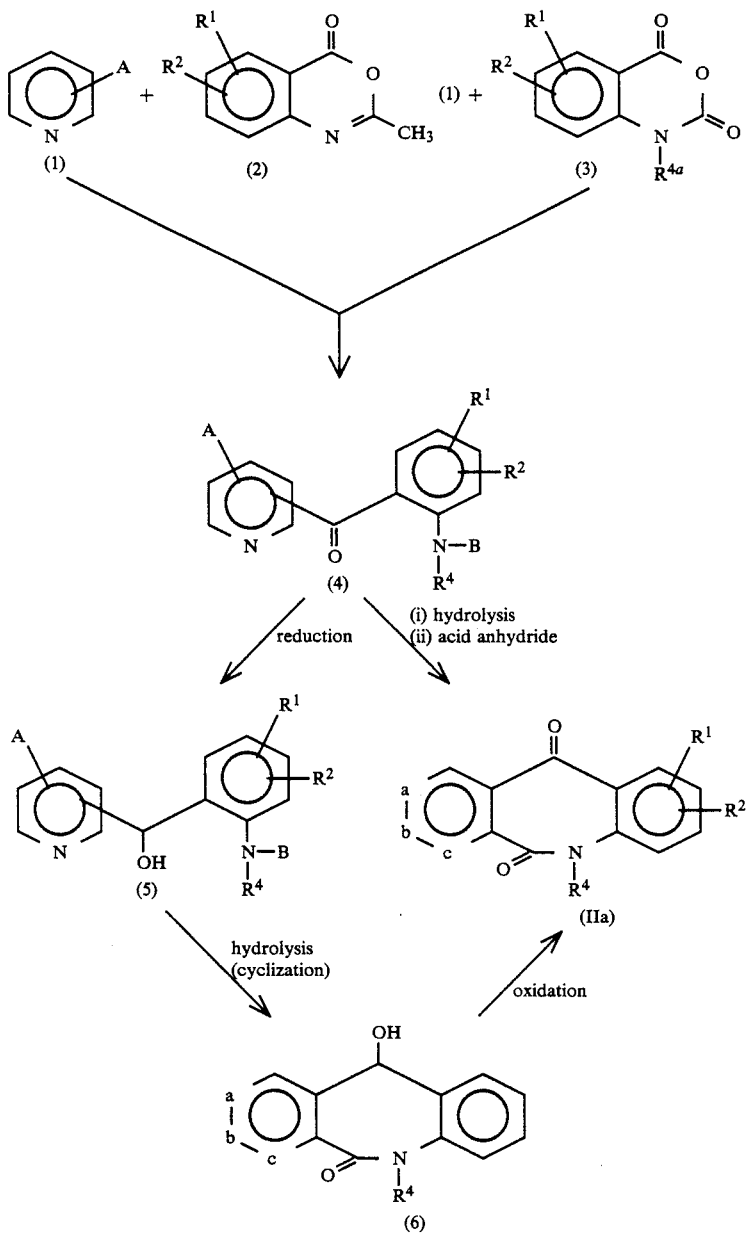

wherein A represents a carboxylic acid equivalent capable of coordinating to a metal; B represents a hydrogen atom or an acetyl group; $R^{4a}$ has the same meaning as $R^4$ except a hydrogen atom; and $R^1$, $R^2$, $R^4$, a, b, and c are as defined above.

−78° to 0° C. for 1 to 10 hours, and then reacted with the compound (2) or (3) at −78° to room temperature for 1 to 10 hours to obtain the compound (4). The reaction is preferably carried, out in a dry inert gas, e.g., nitrogen, argon, and helium. The reaction of the compound (1) with the compound (2) yields the compound (4) wherein B is an acetyl group, and that with the compound (3) yields the compound (4) wherein B is a hydrogen atom.

The compound (4) is reduced in an alcohol, e.g., methanol, in the presence of 0.5 to 5 equivalents of a reducing agent, e.g., sodium borohydride, at a temperature of from 0° C. to room temperature for 1 to 24 hours to obtain the compound (5).

The compound (5) is hydrolyzed and cyclized by an appropriate hydrolysis method, such as reaction in a lower alcohol (e.g., methanol, ethanol) or a mixed solvent of a lower alcohol and water in the presence of an equivalent or excess of an acid (e.g., hydrochloric acid, sulfuric acid) at a temperature of from room temperature up to the boiling point of the solvent for 1 to 24 hours to obtain the compound (6).

The compound (6) is oxidized in acetone or a mixed solvent of acetone and dimethyformamide, etc., in the presence of excess Jones reagent at 0° C. to room temperature for 1 to 24 hours to obtain the compound (IIa).

Alternatively, the compound (4) is hydrolyzed by an appropriate hydrolysis method, for example, reaction in a lower alcohol (e.g., methanol, ethanol) or a mixed solvent of a lower alcohol and water in the presence of an equivalent or excess of an acid (e.g., hydrochloric acid, sulfuric acid) or an alkali (e.g., sodium hydroxide, potassium hydroxide) at a temperature of from room temperature to the boiling point of the solvent for 1 to 48 hours, and then reacted with an acid anhydride (e.g., acetic anhydride) in the presence of a base (e.g., pyridine) at 0° C. to room temperature to thereby obtain the compound (IIa).

Process 1-2

Preparation of Compound (IIb)

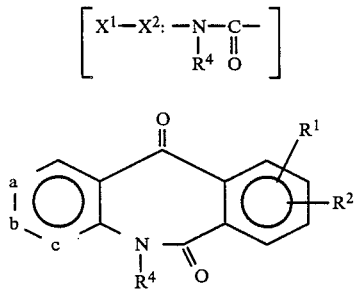

wherein $R^1$, $R^2$, $R^4$, a, b, and c are as defined above.

The compound (IIb) can be synthesized according to the following reaction scheme:

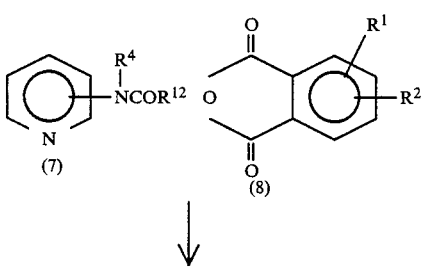

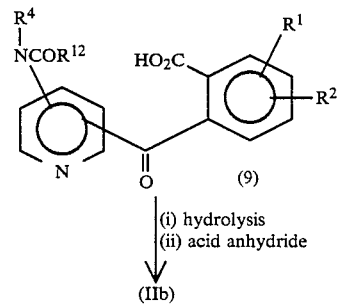

wherein $R^{12}$ represents a lower alkyl group; and $R^1$, $R^2$, $R^4$, a, b, and c are as defined above.

The term "lower alkyl group" as referred to herein is as defined above.

The compound (7) is reacted with 1 to 2 equivalents of an alkyl metal (e.g., lithium diisopropylamide, n-butyl lithium) in an inert solvent, such as ethers (e.g., diethyl ether, tetrahydrofuran) at −78° to 0° C. for 1 to 10 hours and then reacted with the compound (8) at −78° C. to room temperature for 1 to 10 hours to obtain the compound (9). This reaction is preferably carried out in a dry inert gas atmosphere (e.g., nitrogen, argon, helium).

The compound (IIb) can then be obtained from the compound (9) through the same reaction route as Process 1-1 for obtaining the compound (IIa) from the compound (4), i.e., hydrolysis followed by cyclization using an acid anhydride.

Process 1-3

Preparation of Compound (IIc)

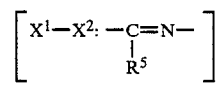

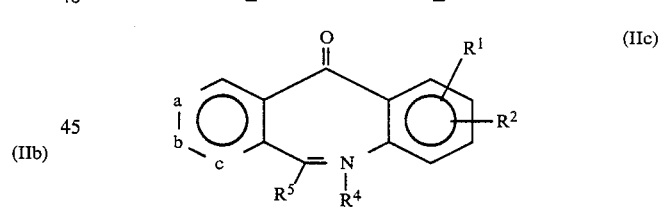

wherein $R^1$, $R^2$, $R^5$, a, b, and c are as defined above.

The compound (IIc) can be synthesized from compound (IIa-2) [compound (IIa) wherein $R^4$ is a hydrogen atom] according to the following reaction scheme:

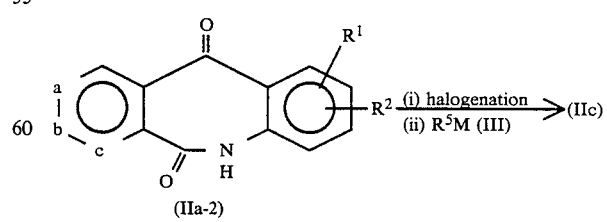

wherein $R^1$, $R^2$, $R^5$, a, b, and c are as defined above; and M represents a hydrogen atom or an alkali metal.

The alkali metal for M includes lithium, sodium, and potassium.

The compound (IIc) can be obtained by reacting the compound (IIa-2) with 1 to 5 equivalents of a halogenating agent (e.g., thionyl chloride, phosphorus oxychloride, phosphorus tribromide) in an inert solvent (e.g., chloroform, methylene chloride) in the presence or absence of a base (e.g., pyridine) at a temperature of from room temperature to the boiling point of the solvent for 1 to 48 hours and then reacting the product with an equivalent to excessive amount of the compound (III) at 0° C. to the boiling point of the solvent for 1 to 10 hours. In the above reaction, the base may also serve as a solvent.

Process 1-4

Preparation of Compound (IId)

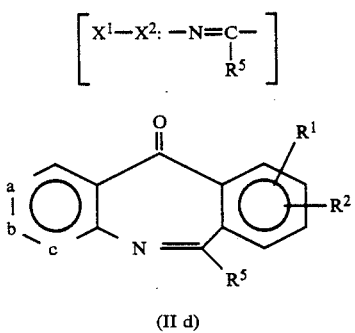

(II d)

wherein $R^1$, $R^2$, $R^5$, a, b, and c are as defined above.

The compound (IId) can be synthesized from compound (IIb 2) [compound (IIb) wherein $R^4$ is a hydrogen atom] according to the following reaction scheme:

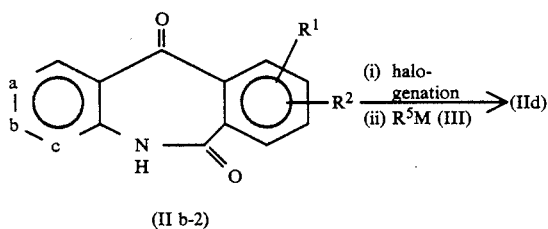

wherein $R^1$, $R^2$, $R^5$, M, a, b, and c are as defined above.

The reaction can be carried out in the same manner as described in Process 1-3.

Process 1-5

Preparation of Compound (IIe)

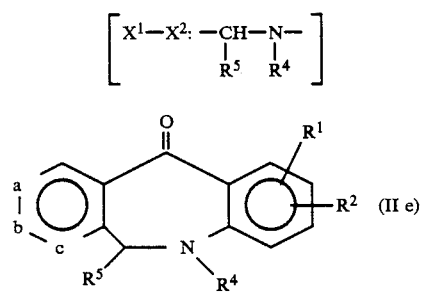

wherein $R^1$, $R^2$, $R^4$, $R^5$, a, b, and c are as defined above.
The compound (IIe) can be synthesized from the compound (IIc) according to the following reaction scheme:

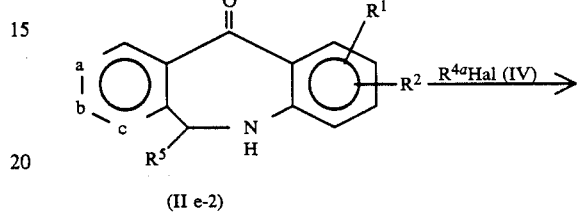

(II c)

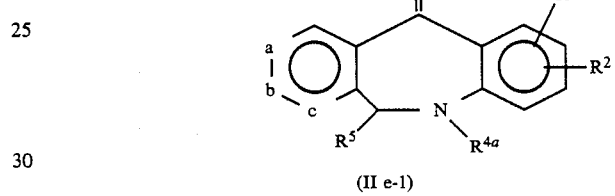

(II e-2)

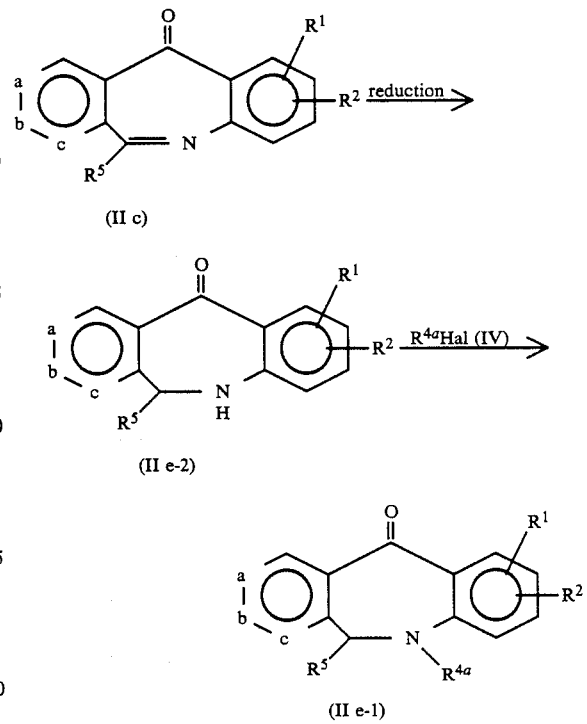

(II e-1)

wherein $R^1$, $R^2$, $R^{4a}$, $R^5$, a, b, and c are as defined above; and Hal represents a halogen atom.

The term "halogen" as used herein includes chlorine, bromine, and iodine atoms.

The compound (IIc) is reduced in an inert solvent such as alcohols (e.g., ethanol) in the presence of a reducing catalyst (e.g., palladium-on-carbon, Raney nickel, platinum dioxide) at a temperature of from room temperature to the boiling point of the solvent for 1 to 24 hours while blowing hydrogen into the reaction system to thereby obtain the compound (IIe-2) [compound (IIe) wherein $R^4$ is hydrogen].

The compound (IIe-2) wherein $R^5$ is a hydrogen atom can also be obtained by reducing the compound (IIc) wherein $R^5$ is a lower alkylthio group.

The compound (IIe-2) may also be obtained by reducing the compound (IIc) in an inert solvent such as alcohols (e.g. methanol, ethanol) with an equivalent of a reducing agent (e.g., sodium cyanoborohydride, sodium borohydride).

The compound (IIe-1) [compound (IIe) wherein $R^4$ is a group other than hydrogen] can be obtained by reacting the compound (IIe-2) with the compound (IV) in the presence or absence of a base (e.g., sodium hydride, potassium carbonate).

Process 1-6

Preparation of Compound (IIf)

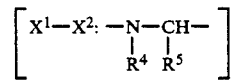

-continued

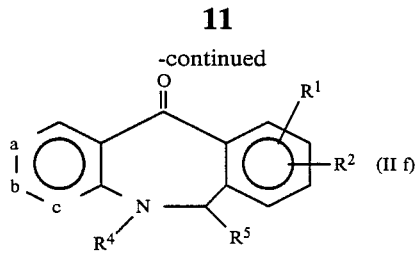

wherein $R^1$, $R^2$, $R^4$, $R^5$, a, b, and c are as defined above.

The compound (IIf) can be synthesized from the compound (IId) according to the following reaction scheme:

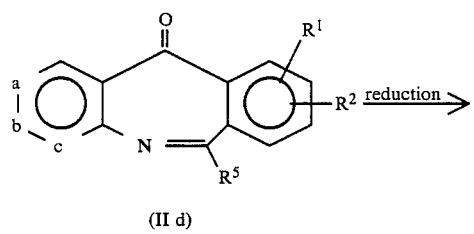

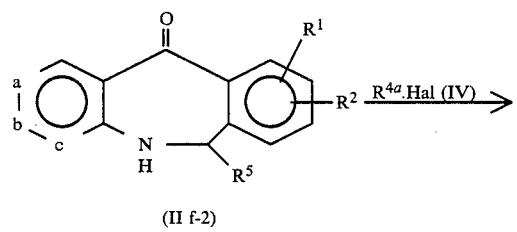

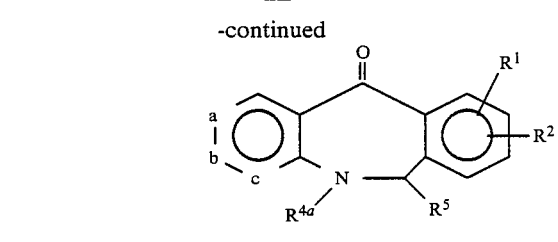

wherein $R^1$, $R^2$, $R^{4a}$, $R^5$, a, b, c, and Hal are as defined above.

The compound (IIf-2) [compound (IIf) wherein $R^4$ is hydrogen] and the compound (IIf-1) [compound (IIf) wherein $R^4$ is a group other than hydrogen] can be obtained in the same manner as described in Process 1-5.

Process 1-7

Preparation of Compound (IIg)

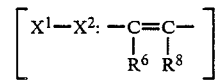

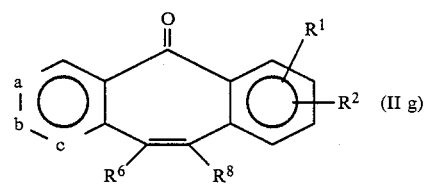

wherein $R^1$, $R^2$, $R^6$, $R^8$, a, b, and c are as defined above.

The compound (IIg) can be synthesized according to the following reaction scheme:

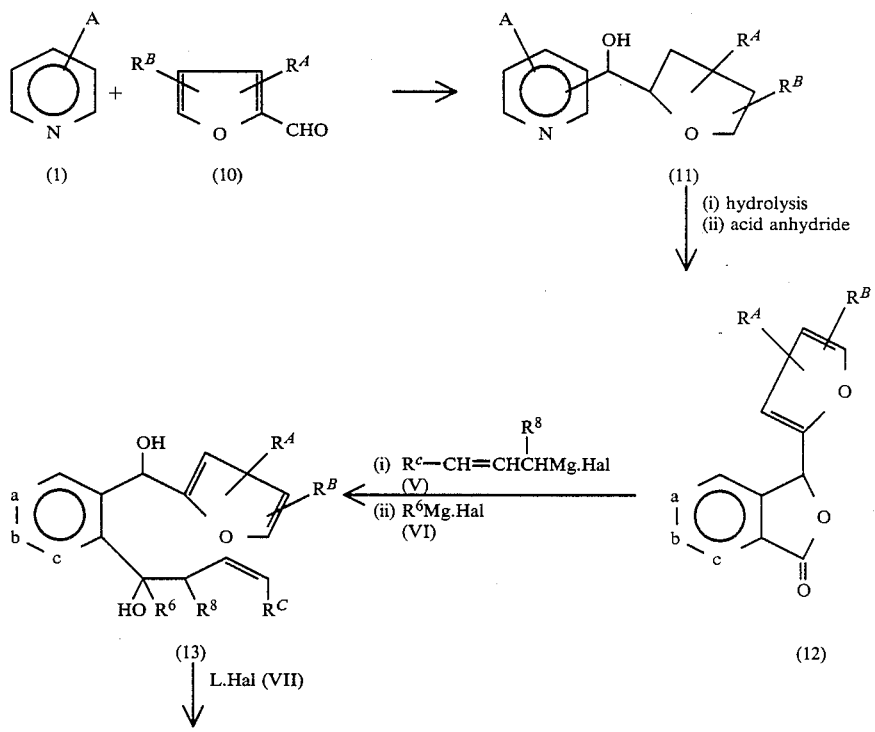

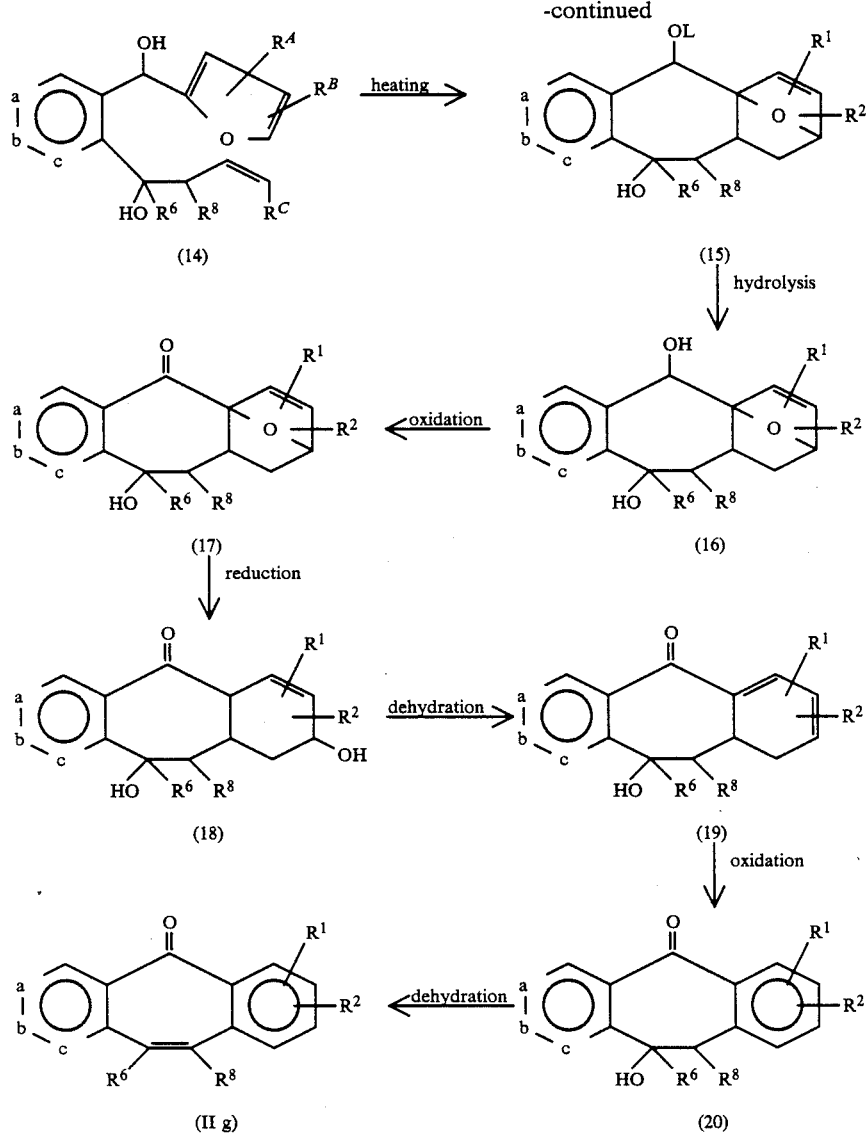

wherein two of $R^A$, $R^B$, and $R^C$ represent $R^1$ and $R^2$, respectively, with the other one representing a hydrogen atom; L represents a protective group for a hydroxy group; and A, $R^1$, $R^2$, $R^6$, $R^8$, a, b, c, and Hal are as defined above.

The protective group as represented by L includes a lower alkyl group, a lower alkanoyl group, and a silyl group (e.g., trimethylsilyl, t-butyldimethylsilyl). The term "alkyl" in "lower alkyl" and "lower alkanoyl" is as defined above.

The reaction between the compounds (1) and (10) to obtain the compound (11) and the reaction for obtaining the compound (12) from the resulting compound (11) can be effected in the same manner as described in Process 1-2.

The compound (13) can be obtained by reacting the compound (12) with an equivalent of Grignard reagent (V) in an inert solvent such as ethers (e.g., diethyl ether, tetrahydrofuran) at 0° C. to room temperature, if necessary, followed by similarly reacting with 1 to 5 equivalents of Grignard reagent (VI) at 0° C. to room temperature.

The compound (13) is then reacted with a hydroxy group-protecting agent (VII), such as alkyl halides, lower alkanoyl halides, and organosilyl halides, in the presence of an appropriate base to obtain the compound (14). For example, the compound (14) wherein L is a t-butyldimethylsilyl group can be obtained by reacting the compound (13) with t-butyldimethylsilyl chloride (VII) in dimethylformamide in the presence of a base (e.g., imidazole) at 0° C. to room temperature.

The compound (14) is heated in an appropriate inert high-boiling solvent (e.g., o-dichlorobenzene) at 150° to 250° C. for 1 to 96 hours to obtain the compound (15).

The compound (16) can be obtained by removing the protective group of the compound (15) through hydrolysis. For example, the compound (15) wherein L is a lower alkyl or lower alkanoyl group is hydrolyzed in a lower alcohol (e.g., methanol, ethanol) or a mixed solvent of a lower alcohol and water in the presence of an equivalent to excessive amount of an acid (e.g., hydrochloric acid, sulfuric acid) at room temperature to the boiling point of the solvent for 1 to 48 hours. The compound (15) wherein L is a t-butyldimethylsilyl group is reacted with a fluorine compound (e.g., tetra-n- butylammonium fluoride) in a solvent such as ethers (e.g., tetrahydrofuran) at 0° to 50° C.

The resulting compound (16) is reacted with an appropriate oxidizing agent such as Jones' reagent in dimethylformamide or a mixed solvent of dimethylformamide and acetone at 0° C. to room temperature for 1 to 48 hours to obtain the compound (17).

The compound (17) is reacted with an appropriate reducing agent such as a zinc powder in the presence of an acid catalyst, preferably in acetic acid, at 0° C. to room temperature for 1 to 5 hours to obtain the compound (18).

The compound (19) can be obtained by dehydration of the compound (18). For example, the dehydration reaction is carried out in an inert solvent (e.g., chloroform, toluene) in the presence of an appropriate acid catalyst (e.g., p-toluenesulfonic acid) at room temperature to the boiling point of the solvent for 1 to 24 hours.

The compound (19) is then oxidized with an appropriate oxidizing agent (e.g., manganese dioxide) in an inert solvent (e.g., chloroform, toluene) at room temperature to the boiling point of the solvent for 1 to 72 hours to obtain the compound (20).

The resulting compound (20) is dehydrated by reaction in sulfuric acid either alone or in combination with an appropriate solvent (e.g., acetic acid) at room temperature to the boiling point of the solvent for 1 to 24 hours to obtain the desired compound (IIg).

Process 1-8a

Preparation of Compound (IIh-1)

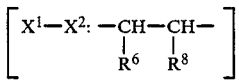

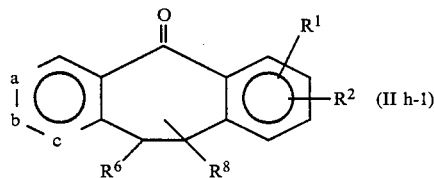

wherein $R^1$, $R^2$, $R^6$, $R^8$, a, b, and c are as defined above.

The compound (IIh-1) can be synthesized by reducing the compound (IIg).

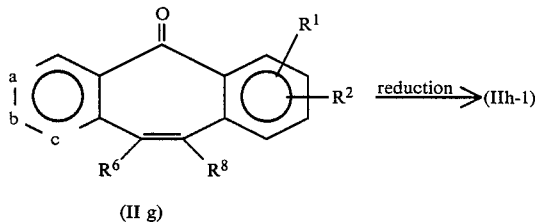

The reaction can be achieved by an appropriate reduction method. For example, the compound (IIg) is reacted in a lower alcohol (e.g., ethanol) in the presence of an appropriate catalyst (e.g., palladium-on-carbon) at 0° to 50° C. for 1 to 24 hours in a hydrogen atmosphere of 1 to 10 atms.

Process 1-8b

Preparation of Compound (IIh-2)

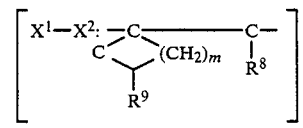

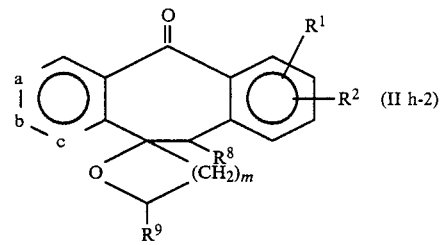

wherein $R^1$, $R^2$, $R^8$, $R^9$, a, b, c, and m are as defined above.

The compound (IIh-2) can be obtained according to the following reaction scheme:

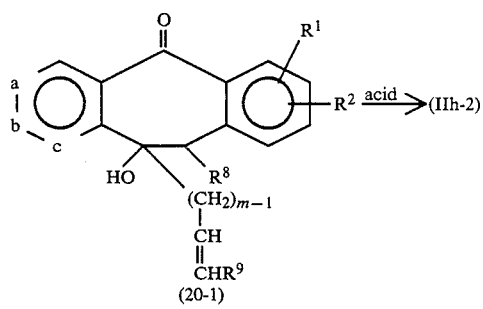

wherein $R^1$, $R^2$, $R^8$, $R^9$, a, b, c, and m are as defined above.

The compound (20-1) [compound (20) wherein $R^6$ is $-(CH_2)_{m-1}-CH=CHR^9$ ($R^9$ and m are as defined above) (as obtained in Process 1-7] is reacted with an appropriate acid (e.g., sulfuric acid) either alone or in combination with an appropriate solvent (e.g., acetic acid) at room temperature to the boiling point of the solvent for 1 to 24 hours to obtain the compound (IIh-2).

Process 1-9

Preparation of Compound (II-A): [any one of a, b, and c is N-oxide]

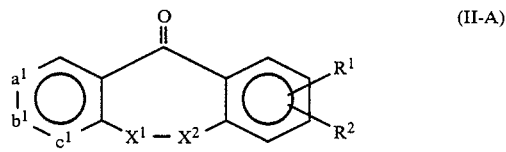

wherein $X^1-X^2$, $R^1$, and $R^2$ are as defined above; and any one of $a^1$, $b^1$, and $c^1$ represents an N-oxide moiety, with the other two each representing a carbon atom.

The compound (II-A) can be synthesized in accordance with the following reaction scheme:

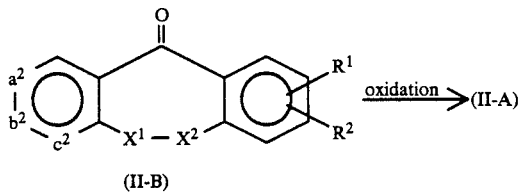

wherein $R^1$, $R^2$, $a^2$, $b^2$, and $c^2$ are as defined above; and any one of $a^2$, $b^2$, and $c^2$ represents a nitrogen atom, with the other two each representing a carbon atom.

The compound (II-B) containing a pyridine ring is reacted with 1 to 5 equivalents of a peroxide (e.g., m-chloroperbenzoic acid, hydrogen peroxide) in an inert solvent (e.g., methylene chloride, chloroform) either alone or, if desired, in combination with a saturated sodium bicarbonate aqueous solution to make a heterogeneous system at 0° C. to room temperature for 1 to 5 hours to thereby obtain the compound (II-A) containing a pyridine-N-oxide ring.

Synthesis of the compound (I) according to the present invention will be illustrated below, but the processes for preparing the compound (I) are not limited to the following processes.

Process 2-1

Preparation of Compound (I-C)[----: double bond]

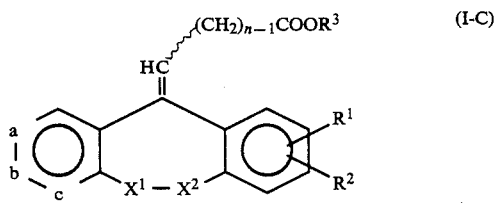

wherein $X^1$—$X^2$, $R^1$, $R^2$, $R^3$, a, b, c, and n are as defined above.

The compound (I-C) can be synthesized from the compound (II) in accordance with the following reaction scheme:

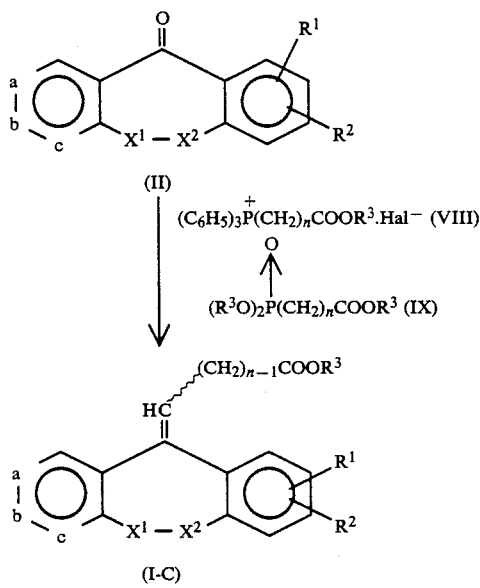

wherein $X^1$—$X^2$, $R^1$, $R^2$, $R^3$, Hal, a, b, c, and n are as defined above.

The compound (I-C) can be obtained by reacting the compound (II) with the compound (VIII) or (IX) in an inert solvent in the presence of a base. The base to be used includes n-butyl lithium, lithium diisopropylamide, sodium hydride, potassium hydride, potassium t-butoxide, and sodium amide, with n-butyl lithium and lithium diisopropylamide being preferred. The inert solvent to be used includes diethyl ether, tetrahydrofuran, dimethyl sulfoxide, and dimethylformamide, either alone or in combinations thereof.

The reaction is preferably carried out in a dry inert gas atmosphere, e.g., nitrogen, argon and helium. The reaction is usually effected at a temperature of from −78° to 30° C. for a period of from 1 to 6 hours.

Process 2-2

Preparation of Compound (I-D) [────: single bond]

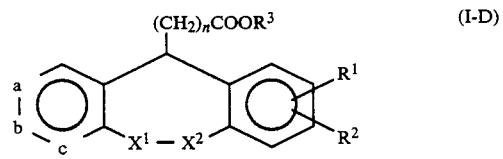

wherein $X^1$-$X^2$, $R^1$, $R^2$, $R^3$, a, b, c, and n are as defined above.

The compound (I-D) can be synthesized from the compound (I-C) as follows.

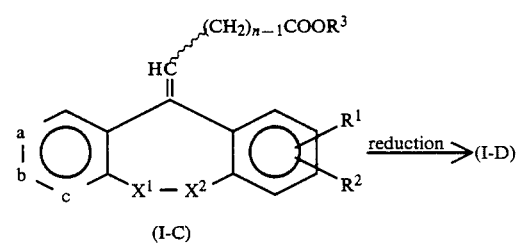

wherein $X^1$-$X^2$ $R^1$, $R^2$ $R^3$, a, b, c, are as defined above.

The compound (I-D) can be obtained by reduction of the compound (I-C). The reduction reaction can be carried out by blowing hydrogen into a reaction system containing the compound (I-C), an alcohol solvent (e.g., ethanol), and a catalyst (e.g., palladium-on-carbon, Raney nickel, platinum dioxide) at room temperature to the boiling point of the solvent for 1 to 24 hours. This reaction is usually attended by reduction of the unsaturated bond in the $X^1$-$X^2$ moiety, i.e.,

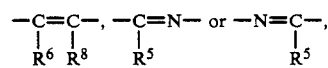

to produce the corresponding compound having a single bond, i.e.,

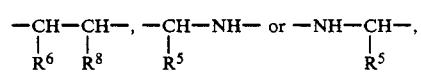

respectively.

Process 2-3

Preparation of Compound- (Ia-1)

$$[X^1-X^2: -\underset{\underset{R^{4a}}{|}}{\underset{\|}{C}}-N-]$$

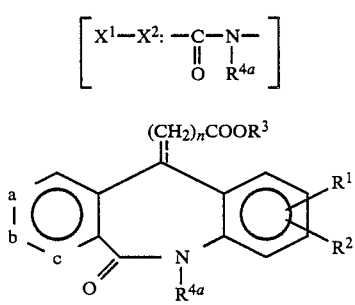
(Ia-1)

wherein $R^1$, $R^2$, $R^3$, $R^{4a}$, a, b, c, and n are as defined above.

The compound (Ia-1) can be synthesized from the compound (Ic-1) through the following reaction scheme:

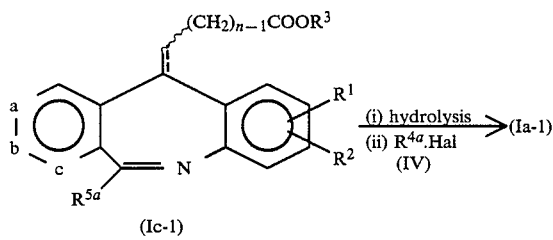
(Ic-1)

wherein $R^1$, $R^2$, $R^3$, $R^{4a}$, a, b, c, Hal, and n are as defined above; and $R^{5a}$ has the same meaning as $R^5$ except for a hydrogen atom.

The compound (Ic-1) is hydrolyzed in a lower alcohol (e.g., methanol, ethanol, propanol) in the presence of an acid catalyst (e.g., p-toluenesulfonic acid, hydrochloric acid) at room temperature to the boiling point of the solvent for 1 to 24 hours. The hydrolysis product is then reacted with the compound (IV) in a solvent, such as ethers (e.g., tetrahydrofuran) and dimethylformamide, in the presence or absence of a base (e.g., sodium hydride, potassium carbonate) to obtain the compound (Ia-1).

Process 2-4

Preparation of Compound (Ib-1)

$$[X^1-X^2: -\underset{\underset{R^{4a}}{|}}{N}-\underset{\|}{\underset{O}{C}}-]$$

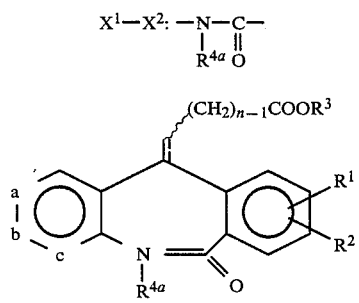
(Ib-1)

wherein $R^1$, $R^2$, $R^3$, $R^{4a}$, a, b, c, and n are as defined above.

The compound (Ib-1) can be synthesized from compound (Id-1) as shown below in the same manner as described in Process 2-3.

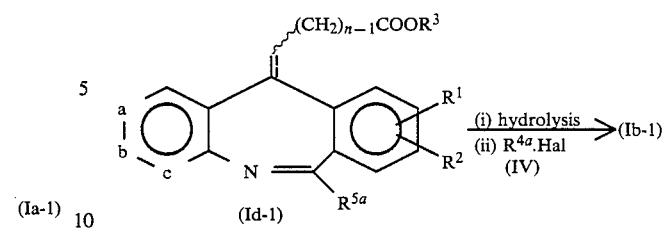
(Id-1)

wherein $R^1$, $R^2$, $R^3$, $R^{4a}$, $R^{5a}$, a, b, c, n, and Hal are as defined above.

Process 2-5

Preparation of Compound (Ic-3)

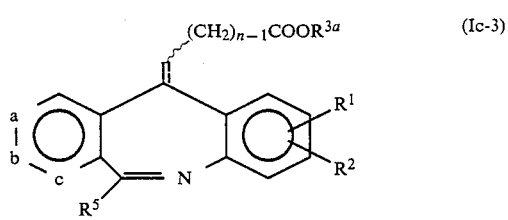
(Ic-3)

wherein $R^{3a}$ has the same meaning as $R^3$ except for a hydrogen atom; and $R^1$, $R^2$, $R^3$, $R^5$, a, b, c, and n are as defined above.

The compound (Ic-3) can be synthesized from compound (Ia-2) as shown below in the same manner as described in Process 1-3.

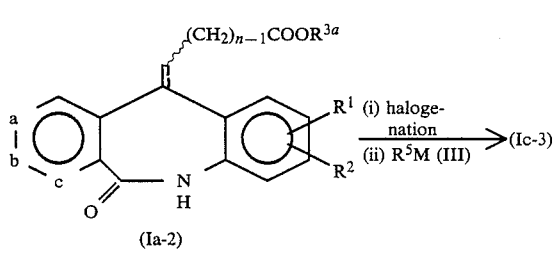
(Ia-2)

wherein $R^1$, $R^2$, $R^{3a}$, $R^5$, M, a, b, c, and n are as defined above.

Process 2-6

Preparation of Compound (Id-3)

$$[X^1-X^2: -N=\underset{\underset{R^5}{|}}{C}-]$$

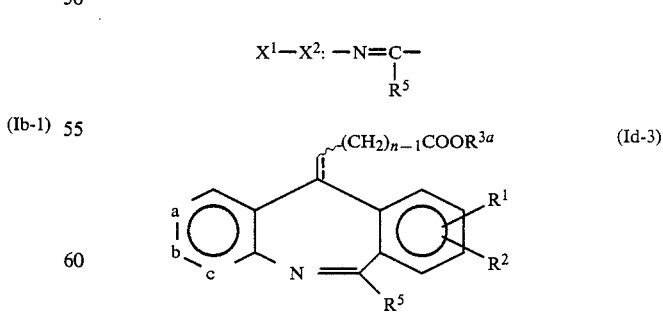
(Id-3)

wherein $R^1$, $R^2$, $R^{3a}$, $R^5$, a, b, c, and n are as defined above.

The compound (Id-3) can be synthesized from compound (Ib-2) as shown in the following reaction scheme in the same manner as described in Process 1-4.

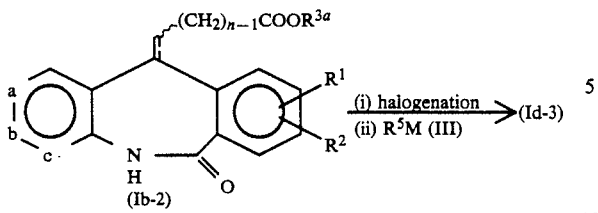

wherein $R^1$, $R^2$, $R^3$, $R^{4a}$, $R^5$, M, a, b, c, and n are as defined above.

Process 2-7

Preparation of Compound (Ie)

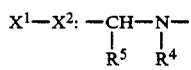

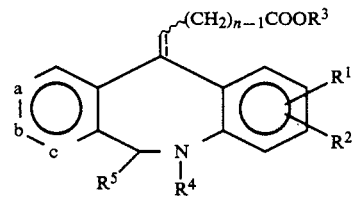

wherein $R^1$, $R^2$, $R^3$, $R^4$, $R^5$, a, b, c, and n are as defined above.

The compound (Ie), including compounds (Ie-1) and (Ie-2), can be synthesized from compound (Ic) in the same manner as in Process 1-5 as shown in the following reaction scheme:

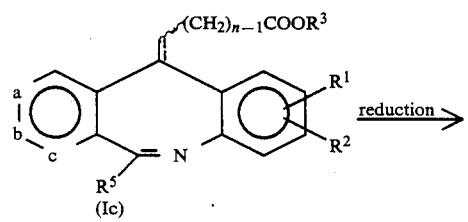

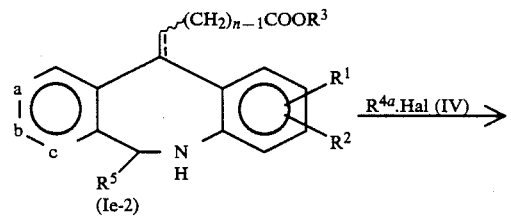

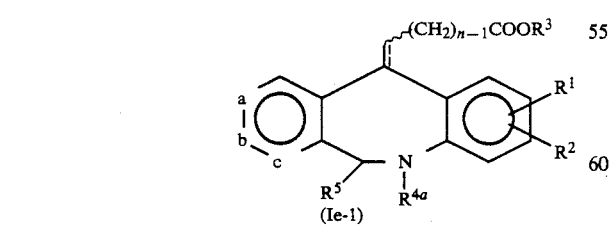

wherein $R^1$, $R^2$, $R^3$, $R^{4a}$, $R^5$, a, b, c, Hal, and n are as defined above.

Process 2-8

Preparation of Compound (If)

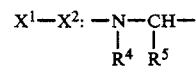

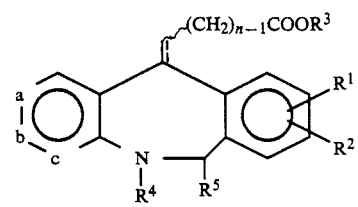

wherein $R^1$, $R^2$, $R^3$, $R^4$, $R^5$, a, b, c, and n are as defined above.

The compound (If), including compounds (If-1) and (If-2), can be synthesized from compound (Id) in accordance with the following reaction scheme:

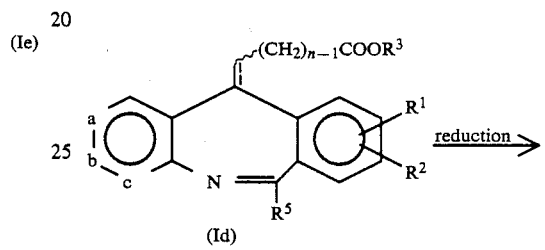

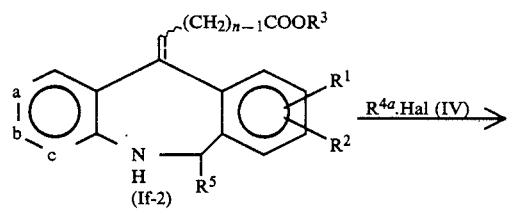

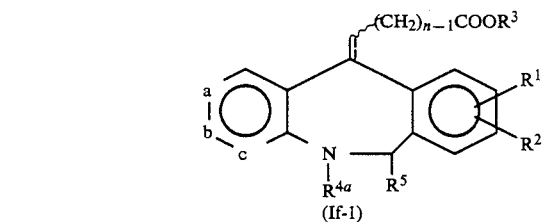

wherein $R^1$, $R^2$, $R^3$, $R^4$, $R^5$, a, b, c, Hal, and n are as defined above.

The reactions can be carried out in the same manner as in Process 1-5.

Process 2-9

Preparation of Compound (I-A) [any one of a, b, and c: N-oxide]

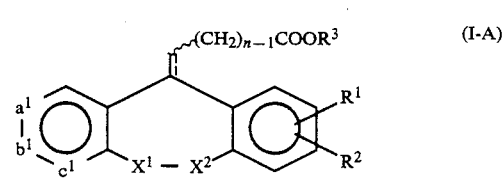

wherein $X^1$-$X^2$, $R^1$, $R^2$, $R^3$, $a^1$, $b^1$, $c^1$, and n are as defined above.

The compound (I-A) containing an N-oxide ring can be synthesized from compound (I-B) containing a pyridine ring in the same manner as described in Process 1-9 as shown by the following reaction scheme:

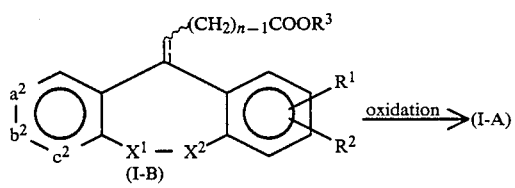

wherein $X^1$-$X^2$, $R^1$, $R^2$, $R^3$, $a^2$, $b^2$, $c^2$ and n are as defined above.

Process 2-10

Preparation of Compound (I-E) [$R^3$: H]

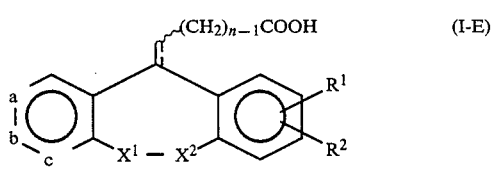

wherein $X^1$-$X^2$, $R^1$, $R^2$, a, b, c, and n are as defined above.

The compound (I-E) can be synthesized from compound (I-F) according to the following reaction scheme:

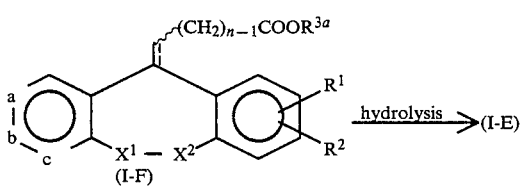

wherein $X^1$-$X^2$, $R^1$, $R^2$, $R^{3a}$, a, b, c, and n are as defined above.

The reaction can be carried out by an appropriate hydrolysis method. For example, the compound (I-F) is hydrolyzed in a lower alcohol (e.g., methanol, ethanol) or a mixed solvent of a lower alcohol and water in the presence of an equivalent to excessive amount of an alkali (e.g., sodium hydroxide, potassium hydroxide) at a temperature of from room temperature to the boiling point of the solvent for 1 to 48 hours.

The intermediates and desired compounds prepared by the above-described processes can be isolated and purified by the methods conventionally used in organic synthesis chemistry such as filtration, extraction with organic solvents (e.g., ethyl acetate, methylene chloride, chloroform), drying, concentration, recrystallization, and various chromatographic technique.

Of the compounds (I) according to the present invention, the compounds (I-C) include geometrical isomers, i.e., E-form and Z-form. The above-described process for synthesizing the compounds (I-C) usually yields mixtures of these isomers, which can be isolated and purified by any means commonly employed in organic synthesis chemistry, such as various chromatographic techniques, recrystallization, and the like.

If desired, the E-form or Z-form may be isomerized to each other. Isomerization can be effected, for example, by treatment in refluxing acetic acid in the presence of an appropriate acid catalyst (e.g., p-toluenesulfonic acid) for 1 to 24 hours.

It should be understood that the present invention includes all the possible stereoisomers of the compounds (I) and mixtures thereof as well as the E/Z isomers as stated.

When it is desired to obtain the compound (I) or (II) in the form of a salt, a product, being obtained as a salt, can be purified as it is, or a product, being obtained as a free form, can be converted to its salt in a usual manner.

The compounds (I) and their pharmacologically acceptable salts according to the present invention inhibit thromboxane synthase obtained by fractionation of solubilized bovine platelet microsome and exhibit potential and long-lasting inhibition of $TXA_2$ biosynthesis in mammals inclusive of humans.

Further, the compounds (I) and their salts have effects to enhance production of prostaglandin $I_2$ ($PGI_2$) exhibiting arterial smooth muscle relaxing activity, platelet aggregation inhibitory activity, or platelet clot dissociating activity.

Prostaglandin $G_2$ ($PGG_2$) or prostaglandin $H_2$ ($PGH_2$) is an important precursor for synthesizing $TXA_2$, $PGI_2$ and other prostanglandins. The compounds (I) and their salts inhibit enzymes of transforming $PGG_2$ to $TXA_2$ (i.e., $TXA_2$ synthase) at extremely low doses (0.01 to 1 mg/kg), while exhibiting virtually no inhibitory activity on transforming enzymes of physiologically useful $PGI_2$ and other prostaglandins, e.g., $PGI_2$ synthase and synthase of various prostaglandins, rather enhancing bioability of $PGH_2$ or $PGG_2$. For example, they enhance biosynthesis of prostanglandin $D_2$ ($PGD_2$) in platelets or enhance biosynthesis of $PGI_2$ in the presence of vascular endothelial cells.

The compounds (I) and salts thereof thus exhibit selective, potential, and long-lasting inhibitory activity on $TXA_2$ synthase without inhibiting $PGI_2$ synthase, prostaglandin synthase (cyclooxygenase), and synthase of other various prostaglandins.

The compounds (I) and salts thereof are of extremely low toxicity in mice, dogs, etc. and are characterized by broadness between toxicity and the effective doses.

The compounds (I) and salts thereof are of long duration in vivo and are thus expected to stably maintain their inhibitory activity of $TXA_2$ synthase for extended periods of time. It is therefore expected that small dose levels of the compounds (I) or their salts would suffice for therapy with reduced side effects even on continuous administration.

The pharmacological activities of the compounds (I) are described below.

TEST EXAMPLE 1

Acute Toxicity Test

A test compound was given to dd male mice weighing $20 \pm 1$ g (3 mice per group) per os. (p.o.; 300 mg/kg) or intraperitoneally (i.p.; 100 mg/kg). The mortality after 7 days from the administration was considered to determine the minimum lethal dose (MLD). The results obtained are shown in Table 1.

TEST EXAMPLE 2

Test on Inhibition of $TXA_2$ Biosynthesis

A mixture of 70 μl of bovine platelet microsome [protein: 40 μg; 100 mM tris-HCl buffer (pH=7.4)] and 10 μl of a test compound solution (100 mM tris-HCl buffer containing 10% methanol) was allowed to stand at 0° C. for 5 minutes, and 20 μl of a prostaglandin $H_2$ solution (100 mM tris-HCl buffer supplemented with acetone containing 0.1 nmol of prostaglandin $H_2$) was added thereto as a substrate. Five minutes later, addition of 2.9 ml of a reaction terminator [phosphate buffer (pH 7.4) containing 100 mM of OKY-1581 (*J. Med. Chem.*, Vol. 24, p. 1139 (1981))] resulted in cessation of the reaction.

The amount of thromboxane $B_2$ ($TXB_2$) (stable degradation product of $TXA_2$) produced in the system was determined by radioimmunoassay [F. A. Fitzpatrick et al., *Methods in Enzymology*, Vol. 86, p.286 (1982)].

Inhibition of $TXB_2$ synthesis was evaluated by $IC_{50}$ (50% inhibitory concentration) or percent inhibition as calculated from equation described below, and the results obtained are shown in Table 1.

% Inhibition =

$$\left(1 - \frac{\text{Test } TXB_2 \text{ level}^* - \text{blank } TXB_2 \text{ level}^{}}{\text{Control } TXB_2 \text{ level}^{*} - \text{blank } TXB_2 \text{ level}}\right) \times 100$$

*$TXB_2$ level when the test compound was added.
**$TXB_2$ level when the reaction was conducted in a system to which the reaction terminator was added before addition of the substrate.
***$TXB_2$ level when no test compound was added.

TABLE 1

| Test Compound | | Acute Toxicity (MLD) | | Inhibition of $TXA_2$ Biosynthesis | |
|---|---|---|---|---|---|
| Example No. | Compound No. | po (mg/kg) | ip (mg/kg) | $IC_{50}$ (μM) | % Inhibition at 10 μM (%) |
| 21 | I-1 | >300 | >100 | 0.032 | |
| 22 | I-2 | >300 | >100 | | 41* |
| 23 | I-3 | >300 | >100 | 0.4 | |
| 24 | I-4 | >300 | >100 | 0.25 | |
| 25 | I-5 | >300 | >100 | 0.13 | |
| 26 | I-6 | >300 | >100 | 0.005 | |
| 27 | I-7 | >300 | >100 | 0.021 | |
| 30 | I-10E | >300 | >100 | 0.021 | |
| 30 | I-10Z | >300 | >100 | 0.016 | |
| 31 | I-11E | >300 | >100 | 0.0083 | |
| 31 | I-11Z | >300 | >100 | 0.041 | |
| 32 | I-12E | >300 | >100 | 0.02 | |
| 32 | I-12Z | >300 | >100 | 0.034 | |
| 33 | I-13E | >300 | >100 | 0.0084 | |
| 33 | I-13Z | >300 | >100 | 0.0035 | |
| 34 | I-14E | >300 | >100 | 0.022 | |
| 35 | I-14Z | >300 | >100 | 0.451 | |
| 36 | I-15 | >300 | >100 | 0.022 | |
| 39 | I-18 | >300 | >100 | 0.1 | |
| 40 | I-19E | >300 | >100 | | 13 |
| 40 | I-19Z | >300 | >100 | | 8 |
| 41 | I-20E | >300 | >100 | | 10 |
| 41 | I-20Z | >300 | >100 | | −23 |
| 42 | I-21 | >300 | >100 | | 47 |
| 43 | I-22 | >300 | >100 | | 27 |
| 43 | I-23 | >300 | >100 | | 27 |

Note: *Percent inhibition at 0.1 μM.

TEST EXAMPLE 3

Test on Inhibition of Silver Nitrate-Induced Arteriothromboembolia in Rats

Male Wistar -Shizuoka rats weighing 270±20 g were anesthetized with urethane (1.5 g/kg) intraperitoneally. Each animal was fixed on its back, and a venous cannula and an arterial cannula were inserted into the left carotid vein and the left femoral artery, respectively. An abdominal incision was made, the intestinal tract was put aside so that the descending abdominal aorta could be seen, the surrounding connective tissues were removed, the descending aorta was detached to a length of about 1 cm, and the detached descending aorta was put on a globe of 8 cm in diameter. A solvent (0.1 ml; physiological saline containing 0.05N sodium hydroxide) or a drug solution (0.1 ml) in the solvent was injected via the cannulated carotid vein per 100 g of body weight. Three minutes later, a 30% silver nitrate aqueous solution was dropped on the detached descending abdominal aorta. Five minutes later, the globe was removed, and the affected site was washed three times with physiological saline to stop the reaction. After the elapse of 30 minutes from the stopping of the reaction, the blood pressure of the femoral artery was measured, and the pressure fall was taken as an indication of obstruction of the descending arterial. Significance of the difference in degree of the obstruction between the control group (only the solvent was administered) and the test group was assayed by $X^2$-assay. The results obtained are shown in Table 2.

TABLE 2

| Drug | Dose (i.v.) (mg/kg) | Number of Obstruction Case/Number of Experiments | Percent Obstruction (%) |
|---|---|---|---|
| Control | — | 23/26 | 88 |
| I-12Z | 0.1 | 4/6 | 67 |
| | 0.3 | 1/5 | 20**3 |
| | 1.0 | 0/5 | 0** |
| | 3.0 | 1/5 | 20** |
| I-13E | 1.0 | 3/4 | 75 |
| | 3.0 | 1/5 | 20** |
| OKY-1581[1] | 0.3 | 5/5 | 100 |
| | 1.0 | 4/6 | 67 |
| | 3.0 | 0/3 | 0** |
| CV-4151[2] | 0.3 | 4/6 | 67 |
| | 1.0 | 4/8 | 50* |

TABLE 2-continued

| Drug | Dose (i.v.) (mg/kg) | Number of Obstruction Case/Number of Experiments | Percent Obstruction (%) |
|---|---|---|---|
|  | 3.0 | 1/5 | 20** |

Note:
[1] product of Ono Pharmaceutical Co., Ltd.
[2] product of Takeda Chemical Industries, Ltd. (both are described in Yuki Gosei Kagaku, 45, 1 (1987).)
[3] *: P < 0.05
**: P < 0.01

Dropping of silver nitrate on the descending aorta caused endothelial disturbances, leading to obstruction. The percent obstruction of the test group having received I-12Z (0.3, 1.0, or 3.0 mg/kg) or I-13E (3 mg/kg) was significantly lower than that of the control group. The I-12Z groups showed inhibition of obstruction at lower doses as compared with the comparative drugs, CV-4151 and OKY-1581.

These test results suggest possibility of usefulness of I-12Z and I-13E in the treatment of thromboembolia.

TEST EXAMPLE 4

Test On Inhibition of Collagen-Induced Ischemic Alterations of Electrocrdiogram Spontaneous hypertensive rats (SHR) (male; 25–30-week-old; available from Hoshino Jikken Dobutsu) were intraperitoneally anesthesized with sodium pentobarbital (60 mg/kg). Each animal was fixed on its back, a venous cannula was inserted into the left jugular vein, and electrocardiograms (ECG) in extremity leads II were taken. A solvent alone (physiological saline containing 0.05N sodium hydroxide) or the test compound (I-12Z or I-13E) dissolved in the same solvent was intravenously administered in an amount of 0.1 ml per 100 g of body weight. Three minutes later, 4.5 mg/kg of collagen III originating from the bovine skin was intravenously injected, and the changes of the ECG were observed over 10 minutes. The ischemic ECG alterations after the intravenous injection of collagen were scored based on the following system according to the method of Matsumura et al., *Folia Pharmacol., Japon,* and the significance of difference in scores of the control group receiving the solvent alone and the test group was examined by the U-test of Mann-Whitney. The results obtained are shown in Table 3.

Score System:
0 ... Changes of 0.05 mV or less in the S-T segment or the T wave
1 ... Changes between 0.05 and 0.1 mV in the S-T segment or the T wave
2 ... Changes of 0.1 mV or more in the S-T segment or the T wave
3 ... Arrythmia or cardiac arrest

TABLE 3

| Time Elapsed After Collagen Injection (min) | Change of ECG | | |
|---|---|---|---|
|  | Control | I-12Z (1 mg/kg, iv) | I-13E (1 mg/kg, iv) |
| 0.5 | 0.5 ± 0.5[1] | 0.8 ± 0.5 | 0 ± 0 |
| 1 | 1.2 ± 0.6 | 0.5 ± 0.2 | 0.2 ± 0.2 |
| 2 | 0.3 ± 0.2 | 1.0 ± 0.4 | 0.2 ± 0.2 |
| 3 | 2.2 ± 0.4 | 0.8 ± 0.3*[2] | 0.2 ± 0.2** |
| 4 | 2.0 ± 0.4 | 0.7 ± 0.2** | 0.6 ± 0.4* |
| 5 | 2.7 ± 0.3 | 0.2 ± 0.2** | 0.2 ± 0.2** |
| 6 | 2.2 ± 0.4 | 0.3 ± 0.2** | 0.4 ± 0.2** |
| 7 | 2.7 ± 0.3 | 0.5 ± 0.2** | 0.4 ± 0.2** |
| 8 | 2.3 ± 0.5 | 0.5 ± 0.2* | 0.4 ± 0.2* |
| 9 | 2.5 ± 0.3 | 0.4 ± 0.2** | 0.4 ± 0.2* |
| 10 | 2.2 ± 0.5 | 0.3 ± 0.2** | 0.2 ± 0.2* |

Note:
[1]: Mean Standard Error (N = 5 to 6)
[2]: *: P < 0.05; **: P < 0.01

As can be seen from Table 3, intravenous administration of collagen to SHR induced ischemic ECG changes, while the ECG changes in animals receiving 1 mg/kg of I-12Z or I-13E were significantly smaller than those in the control groups receiving the solvent alone. These results imply the possibility of usefulness of I-12Z and I-13E in the treatment of angina pectoris.

The compounds (I) and pharmacologically acceptable salts thereof may be administered alone, but, in general, are preferably administered in the form of various preparations. The preparations are usable in animals and humans.

The preparations according to the present invention contain the compound (I) or a pharmacologically acceptable salt thereof as an active ingredient either alone or, if desired, in combination with other active ingredients for the purposed treatment. The preparations can be prepared by mixing the active ingredient(s) with one or more of pharmaceutically acceptable carriers and formulating into various dose forms according to any means well known in the art.

The active ingredients which may be used in combination with the compounds (I) or their salts include steroids, non-steroid antiinflammatory agents, peripheral analgesics, leukotriene antagonists, leukotriene biosynthesis inhibitors, $H_2$-receptor antagonists, antihistaminics, histamin-release inhibitors, bronchodilators, angiotensin converting enzyme inhibitors, thromboxane $A_2$ biosynthesis inhibitors, $H^+$-$K^+$ATPase inhibitors, coronary vasodilators, calcium antagonists, diuretics, xanthine oxidase inhibitors, cerebral circulation improving agents, cerebral metabolism activators, cerebral protectives, antiplatelets, thrombolytics, adrenergic α-receptor antagonists, serotonin antagonists, platelet activation factor (PAF) antagonists, and so on.

The administration route is preferably selected so as to result in the most effective therapy and includes oral administrations and non-oral administrations, such as rectal, topical, intranasal, intra-ocular, intra-oral, subcutaneous, intramuscular, and intravenous administrations.

The dose forms of the preparations include capsules, tablets, granules, powders, syrups, emulsions, suppositories, ointments, eye drops, nose drops, troches, aerosols, and injections.

Liquid preparations suitable for oral administrations, such as emulsions and syrups, can be prepared by using water, saccharides (e.g., sucrose, sorbitol, fructose), glycols (e.g., polyethylene glycol, propylene glycol), oils (e.g., sesami oil, olive oil, soybean oil), preservatives (e.g., p-hydroxybenzoic esters), and flavors (e.g., strawberry flavor, peppermint flavor). Capsules, tablets, powders, and granules can be prepared by using vehicles (e.g., lactose, glucose, sucrose, mannitol), disintegrators (e.g., starch, sodium alginate), lubricants (e.g., magnesium stearate, talc), binders (e.g., polyvinyl alcohol, hydroxypropyl cellulose, gelatin), surface active agents (fatty acid esters), and plasticizers (e.g., glycerin).

Preparations suitable for non-oral administration preferably comprise an active compound-containing sterilized aqueous solution which is isotonic to the blood of a patient. For example, an injectable solution is prepared by using a carrier comprising a salt solution, a glucose solution, or a mixture thereof.

Nasal sprays comprise an isotonic solution of the active ingredient in purified water which contains a preservative. The nasal preparations should be adjusted to a pH compatible to the nasal membrane as well as be made isotonic to the nasal membrane.

Ocular preparations are prepared in the same manner as for nasal sprays except that the pH and isotonic factors should be adjusted to the eyes.

Topical preparations are prepared by dissolving or suspending the active ingredient in one or more media, such as mineral oils, petroleum, polyhydric alcohols, and other bases commonly used in topical preparations.

Rectal preparations are available as suppositories prepared by using general carriers, e.g., cacao butter, hardened oils, glycerides of saturated fatty acids.

These non-oral preparations may further contain one or more adjuvants useful in oral preparations, such as diluents, flavors, preservatives (inclusive of antioxidants), vehicles, disintegrators, lubricants, binders, surface active agents, and plasticizers.

The effective dose and schedules for the administration of the compound (I) or a pharmacologically acceptable salt thereof vary depending on the administration route, the age and body weight of patients, and the symptoms or severity. A recommended administration schedule is 0.01 to 1000 mg/patient/day in a single dose or several divided doses.

The present invention is now illustrated in greater detail with reference to the following Examples but it should be understood that the present invention is not deemed to be limited thereto.

EXAMPLE 1

5,11-Dihydropyrido[4,3-c][1]benzazepin-5,11(6H)-dione [Compound (II-1)]

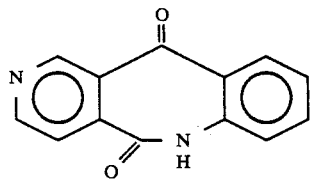

In 200 ml of dry tetrahydrofuran (THF) was dissolved 10.05 g (48 mmol) of N,N-diisopropylisonicotinamide (1a), and to the solution was added dropwise a dry THF solution of lithium diisopropylamide, prepared from 48 ml; (75 mmol) of n-butyl lithium and 11 ml (78 mmol) of diisopropylamine, at −78° C. in a nitrogen stream. After the mixture was stirred at −78° C. for 2 hours, 12.5 g (78 mmol) of 2-methyl-4H-3,1-benzoxazin-4-one (2a) was added thereto, followed by stirring at −78° C. for 1 hour. To the reaction mixture was added 200 ml of water, followed by extraction with 500 ml of chloroform. The extract was washed with a saturated sodium chloride aqueous solution, dried over anhydrous sodium sulfate, and distilled to remove the solvent under reduced pressure. The residue was dissolved in 300 ml of methanol, 3 g (78 mmol) of sodium borohydride was added thereto, and the mixture was stirred at room temperature for 1 hour. After the reaction, the solvent was removed by distillation under reduced pressure, and the residue was subjected to silica gel column chromatography using ethyl acetate as an eluent to obtain 10.4 g (58.4%) of 3-[α-hydroxy-(2-acetylaminobenzyl)]-4-(N,N-diisopropyl)pyridylamide (5a) as a colorless oil.

NMR (CDCl$_3$-CD$_3$OD) δ(ppm): 9.01 & 8.40 (1H, s), 8.57 & 8.50 (1H, d, J=4.9 Hz), 7.83 & 7.73 (1H, d, J=8.0 Hz), 7.36–7.27 (2H, m), 7.13 & 7.06 (1H, d, J=5.9 Hz), 6.15 & 5.97 (1H, s), 3.27–3.75 (2H, m), 2.16 & 2.10 (3H, s), 1.56, 1.54, 1.47, 1.39, 1.20, 1.15, 1.08 & 0.43 (12H, d)

MS (m/z): 269 (M+)

In 350 ml of 20% sulfuric acid was dissolved 34.7 g (94 mmol) of the compound (5a), and the solution was heated at 80° C. for 1.5 hours. After cooling, the reaction mixture was neutralized with a 10N sodium hydroxide aqueous solution to obtain 11.2 g (52.7%) of 11-hydroxy-5,11-dihydropyrido[4,3-c][1]benzazepin-5(6H)-one (6a) as a colorless crystal.

NMR (DMSO-d$_6$) δ (ppm): 10.78 (1H, s), 8.82 (1H, s), 8.62 (1H, d, J=4.9 Hz), 7.62 (1H, d, J=4.9 Hz), 7.55 (1H, d, J=7.6 Hz), 7.13–7.28 (2H, m), 5.76 (1H, s)

IR (KBr tablet) cm$^{-1}$: 3450, 1670

MS (m/z): 226 (M+)

In 190 ml of dimethylformamide was dissolved 8 g (79.6 mmol) of the compound (6a). To the solution was added 250 ml of acetone, and 19 ml of 4N Jones' reagent was then added thereto dropwise at room temperature. After the mixture was stirred at room temperature for 30 minutes, 100 ml of methanol and excess sodium hydrogencarbonate were added thereto. The solvent was removed by distillation under reduced pressure. To the residue was added 200 ml of water, and the precipitated crystals were collected by filtration to obtain the entitled compound (II-1) in a yield of 9.7 g (54.5%).

NMR (CDCl$_3$) δ(ppm): 9.00 (1H, s), 8.86 (1H, d, J=5 Hz), 8.00 (1H, d, J=5 Hz), 7.65 (1H, dt, J=2 & 8 Hz), 7.15–7.50 (3H, m)

MS (m/z): 224 (M+)

EXAMPLE 2

9-Bromo-5,11-dihydropyrido[4,3-c][1]benzazepin-5,11(6H)dione [Compound (II-2)]

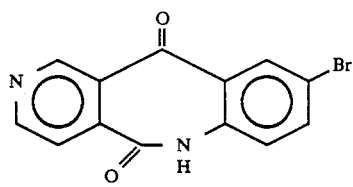

The entitled compound (II-2) was obtained as a colorless crystal from the compound (1a) and 6-bromo-2-methyl-4H-3,1-benzoxazin-4-one (2b) in the same manner as in Example 1.

NMR (DMSO-d$_6$) δ (ppm): 9.05 (1H, bs), 7.15–8.20 (5H, m)

MS (m/z): 304 (M+ +2), 302 (M+)

EXAMPLE 3

9-Acetoxy-5,11-dihydropyrido[4,3-c][1]benzazepin-5,11(6H)-dione [Compound (II-3)]

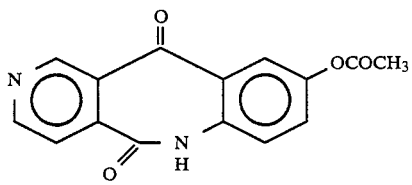

The entitled compound (II-3) was synthesized from the compound (1a) and 6-acetoxy-2-methyl-4H-3,1-benzoxazin-4-one (2c) in the same manner as in Example 1.

NMR (DMSO-$d_6$) δ(ppm): 9.00 (1H, s), 8.93 (1H, d, J=5 Hz), 8.03 (1H, d, J=5 Hz), 7.46 (1H, d, J=8 Hz), 7.43 (1H, d, J=8 Hz), 7.38 (1H, s), 2.28 (3H, s)

EXAMPLE 4

9-Hydroxy-5,11-dihydropyrido[4,3-c][1]benzazepin-5,11(6H)-dione [Compound (II-4)]

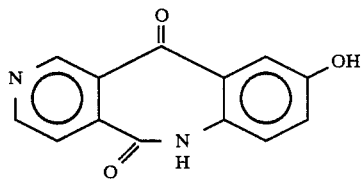

In 100 ml of methanol was dissolved 2.98 g (10.5 mmol) of the compound (II-3) as obtained in Example 3, and 20 ml of a 5% sodium hydroxide aqueous solution was added thereto, followed by stirring at 0° C. for 30 minutes. After completion of the reaction, the reaction mixture was adjusted to a pH of 6.5 with 5% hydrochloric acid. The thus formed crystals were collected by filtration to recover 2.45 g (98.6%) of the entitled compound (II-4) as yellow crystals.

NMR (DMSO-$d_6$) δ(ppm): 9.01 (1H, s), 8.95 (1H, d, J=7 Hz), 8.02 (1H, d, J=7 Hz), 7.05–7.30 (3H, m)

EXAMPLE 5

9-Methoxy-6-methyl-5,11-dihydropyrido[4,3-c][1]benzazepin-5,11(6H)-dione [Compound (II-5)]

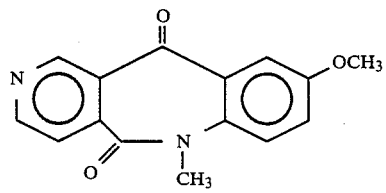

In 50 ml of dimethylformamide was dissolved 1.5 g (6.25 mmol) of the compound (II-4) as obtained in Example 4, and 2.0 g (14.5 mmol) of potassium carbonate and 2.0 g (14.1 mmol) of methyl iodide were added thereto. The mixture was stirred at room temperature for 16 hours in a nitrogen stream. After completion of the reaction, ml of water was added to the reaction mixture, and the mixture was extracted twice with 200 ml portions of chloroform. The extract was dried over anhydrous sodium sulfate, and the solvent was removed by distillation under reduced pressure. The resulting residue was subjected to silica gel column chromatography using chloroform as an eluent to obtain 240 mg (14.5%) of the entitled compound (II-5) as a colorless crystal.

NMR (DMSO-$d_6$) δ(ppm): 8.90 (1H, bs), 6.95–8.00 (5H, m), 3.81 (3H, s), 3.51 (3H, s)

MS (m/z): 268 (M+)

EXAMPLE 6

7-Methyl-5,11-dihydropyrido[4,3-c][1]benzazepin-5,11(6H)-dione [Compound (II-6)]

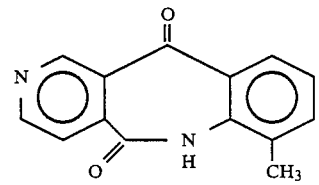

The entitled compound (II-6) was obtained as a colorless crystal from the compound (1a) and 2,8-dimethyl-4H-3,1-benzoxazin-4-one (2d) in the same manner as in Example 1.

NMR (DMSO-$d_6$) δ(ppm): 8.99 (1H, bs), 7.92 (1H, bs), 7.38–7.60 (3H, m), 7.23 (1H, d, J=8 Hz), 2.43 (3H, s)

MS (m/z): 238 (M+)

EXAMPLE 7

6-Benzyl-5,11-dihydropyrido[4,3-c][1]benzazepin-5,11(6H)-dione [Compound (II-7)]

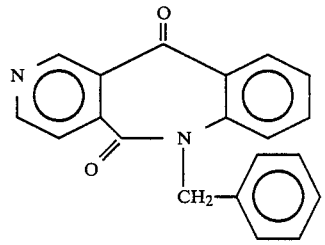

The entitled compound (II-7) was obtained as a colorless crystal from the compound (1a) and N-benzyl isatoic acid anhydride (3a) in the same manner as in Example 1.

NMR (CDCl$_3$) δ(ppm): 8.88 (1H, s), 8.82 (1H, d, J=5 Hz), 7.93 (1H, d, Jz5 Hz), 7.56 (1H, dt, J=2 & 8 Hz), 7.23 (5H, s), 7.10–7.50 (3H, m), 5.30 (2H, s)

IR (CHCl$_3$) cm$^{-1}$: 1655, 1690

MS (m/z): 314 (M+)

EXAMPLE 8

6-Methyl-5,11-dihydropyrido[4,3-c][1]benzazepin-5,11(6H)-dione [Compound (II-8)]

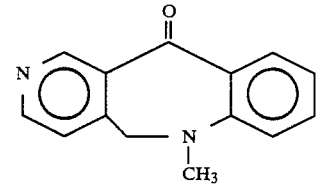

The entitled compound (II-8) was obtained as a colorless crystal from the compound (1a) and N-methylisatoic acid anhydride (3b) in the same manner as in Example 1.

NMR (CDCl$_3$) δ(ppm): 8.90 (1H, s), 8.86 (1H, d, J=5 Hz), 7.95 (1H, d, J=5 Hz), 3.63 (3H, s)

MS (m/z): 238 (M+)

EXAMPLE 9

Compound (II-8) (Alternative Process)

In 2000 ml of dry THF was dissolved 120 g (0.732 mol) of N-isopropylisonicotinamide (1b), and 1000 ml (1.56 mol) of n-butyl lithium was added thereto at −78° C. under a nitrogen stream. After stirring the methylisatoic acid anhydride (3b) was added thereto, followed by stirring at −78° C. for 1 hour. To the reaction mixture was added 500 ml of water, and the mixture was extracted with 3000 ml of chloroform. The extract was washed with a saturated sodium chloride aqueous solution and dried over anhydrous sodium sulfate. The solvent was removed by distillation under reduced pressure. Recrystallization of the residue from ethyl acetate yielded 66 g of N-isopropyl-3-(2-methylamino)benzoylisonicotinamide (4a) as a pale yellow crystal.

NMR (CDCl$_3$) δ(ppm): 8.64 (1H, d, J=5 Hz), 8.54 (1H, s), 7.51 (1H, d, J=5 Hz), 6.28-7.44 (4H, m), 3.6-4.3 (1H, m), 2.94 (3H, d, J=5 Hz), 1.02 (6H, d, J=6 Hz)

MS (m/z): 297 (M+)

In 1000 ml of ethanol was dissolved 150 g (0.51 mol) of the compound (4a), and 300 ml of a 10N sodium hydroxide aqueous solution was added thereto, followed by heating at reflux for 4 hours. The solvent was removed from the reaction mixture by distillation under reduced pressure, and 300 g of ice was added to the residue. The solution was adjusted to a pH of 4.5 with 4N hydrochloric acid. The thus precipitated crystals were collected by filtration and dissolved in 1000 ml of pyridine. To the solution was added 50 ml of acetic anhydride at room temperature, followed by stirring at 50° C. for 2 hours. The solvent was removed by distillation under reduced pressure, the residue was extracted with 1000 ml of chloroform, and the extract was dried over anhydrous sodium sulfate. The solvent was removed by distillation, the residue was subjected to silica gel column chromatography using a 1:1 (by volume) mixture of ethyl acetate and n-hexane as an eluent to obtain 82 g (72%) of the entitled compound (II-8) as a colorless crystal.

EXAMPLE 10

6,11-Dihydropyrido[4,3-c][2]benzazepin-6,11(5H)-dione [Compound (II-9)]

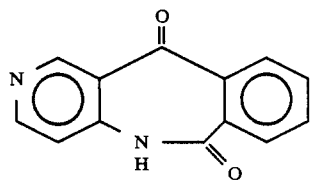

The entitled compound (II-9) was obtained as a colorless crystal from 4-(t-butylcarbonylamino)pyridine (7a) and phthalic anhydride (8a) in the same manner as in Example 9.

NMR (CDCl$_3$-CD$_3$OD) δ(ppm): 8.95 (1H, s), 8.52 (1H, d, J=6 Hz), 7.45-8.35 (4H, m), 7.17 (1H, d, J=6 Hz)

MS (m/z): 224 (M+)

EXAMPLE 11

5-Thiomethylpyrido[4,3-d][1]benzazepin-11(11H)-one [Compound (II-10)]

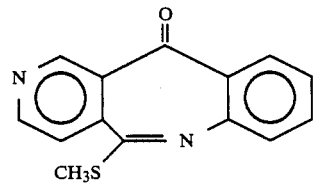

One gram (4.5 mmol) of the compound (II-9) as obtained in Example 10 was dissolved in 20 ml of pyridine, and 2 ml (21.5 mmol) of phosphorus oxychloride was added to the solution, followed by heating at 70° C. for 2 hours while stirring. The solvent was removed by distillation under reduced pressure, and to the residue was added 10 ml of methanol under ice-cooling. To the mixture was further added 5 ml of a sodium methylmercaptan aqueous solution, and the mixture was stirred for 1 hour. The solvent was removed by distillation, and the residue was recrystallized from methanol to obtain 1.04 g (85%) of the entitled compound (II-10) as a colorless crystal.

NMR (CDCl$_3$) δ(ppm): 9.13 (1H, s), 8.93 (1H, d, J=5 Hz), 7.88 (1H, d, J=5 Hz), 7.87 (1H, dd, J=1 & 8 Hz), 7.63 (1H, dt, J=1 & 8 Hz), 7.53 (1H, dd, J=1 & 8 Hz), 7.35 (1H, dt, J=1 & 8 Hz), 2.61 (3H, s) MS (m/z): 254 (M+)

EXAMPLE 12

6-Methoxypyrido[4,3-c][2]benzazepin-11(11H)-one [Compound (II-11)]

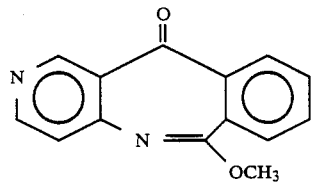

The entitled compound (II-11) was obtained as a colorless crystal from the compound (II-9) as prepared in Example 10 in the same manner as in Example 11, except for replacing the sodium methylmercaptan with sodium methoxide.

NMR (CDCl$_3$) δ(ppm): 8.88 (1H, s), 8.53 (1H, d, J=6 Hz), 7.10-8.10 (5H, m), 4.02 (3H, s)

MS (m/z): 238 (M+)

EXAMPLE 1

5,6-Dihydropyrido[4,3-c][1]benzazepin-11(11H)-one [Compound (II-12)]

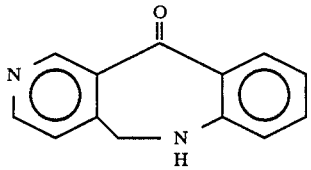

Three grams (11.8 mmol) of the compound (II-10) as obtained in Example 11 were dissolved in 100 ml of ethanol, and 5 g of Raney nickel was added thereto, followed by heating at reflux for 1 hour under a hydrogen stream. The catalyst was separated by filtration, and the filtrate was concentrated under reduced pressure. The residue was purified by silica gel column chromatography using a 1:2 (by volume) mixture of ethyl acetate and n-hexane as an eluent to obtain 0.7 g (28%) of the entitled compound (II-12) as a colorless crystal.

NMR (CDCl$_3$) δ(ppm): 8.95 (1H, s), 8.66 (1H, d, J=5 Hz), 8.18 (1H, d, J=8 Hz), 6.90–7.55 (3H, m), 6.73 (1H, d, J=8 Hz), 4.21 (2H, s)

MS (m/z): 210 (M+)

EXAMPLE 14

5,11-Dihydropyrido[3,4-c][1]benzazepin-5,11(10H)-dione [Compound (II-13)]

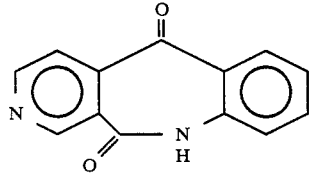

The entitled compound (II-13) was obtained as a colorless crystal from N,N-diisopropylnicotinamide (1c) and 2-methyl-4H-3,1-benzoxazin-4-one (2a) in the same manner as in Example 1.

NMR (DMSO-d$_6$) δ(ppm): 7.10–7.95 (6H, m)
MS (m/z): 224 (M+)

EXAMPLE 15 5,11(10H)-dione [Compound (II-14)]

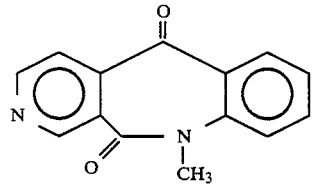

The entitled compound (II-14) was obtained as a colorless crystal from the compound (1c) and N-methylisatoic acid anhydride (3b) in the same manner as in Example 1.

NMR (DMSO-d$_6$) δ(ppm): 9.50 (1H, bs), 7.20–7.80 (6H, m)

MS (m/z): 238 (M+)

EXAMPLE 16

11-Thiomeethylpurido[3,4-c][1]benzazepin-5(5H)-one [Compound (II-15)]

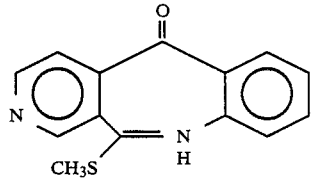

The entitled compound (II-15) was obtained as a colorless crystal from the compound (II-13) as prepared in Example 14 in the same manner as in Example 12.

NMR (CDCl$_3$) δ(ppm): 9 33 (1H, s), 8.88 (1H, d, J=6 Hz), 7.18–8.00 (5H, m), 4.07 (3H, s)

MS (m/z): 238 (M+)

EXAMPLE 17

11-Methoxy-10,11-dihydropyrido[3,4-c][1]benzazepin-5(5H)-one [Compound (II-16)]

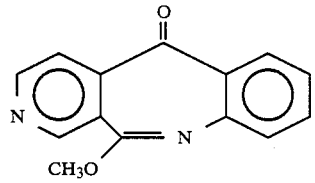

The entitled compound (II-16) was obtained as a colorless crystal from the compound (II-13) as prepared in Example 14 in the same manner as in Example 12.

NMR (CDCl$_3$) δ(ppm): 9.33 (1H, s), 8.88 (1H, d, J=6 Hz), 7.18–8.00 (5H, m), 4.07 (3H, s)

MS (m/z): 238 (M+)

EXAMPLE 18

11-Methoxy-10, 11-dihydropyrio[3,4-c][1]benzazepin-5(5H)-one [Compound (II-17)]

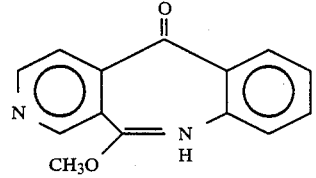

One gram (4.2 mmol) of the compound (II-16) as obtained in Example 17 was dissolved in 20 ml of methanol, and 265 mg (4.3 mmol) of sodium cyanoborohydride was added thereto under ice-cooling while stirring. The stirring was continued for an additional period of 2 hours. The solvent was removed from the reaction mixture by distillation under reduced pressure, and the residue was extracted with 100 ml of chloroform and then dried over anhydrous sodium sulfate. The solvent was removed by distillation, and the residue was purified by silica gel column chromatography using a 1:2 (by volume) mixture of ethyl acetate and n-hexane as an eluent to obtain 0.9 g (90%) of the entitled compound (II-17) as a colorless oil.

NMR (CDCl$_3$) δ(ppm): 8.71 (1H, s), 8.54 (1H, d, J=5 Hz), 7.60 (1H, d, J=5 Hz), 7.15–7.62 (4H, m), 5.04 (1H, s), MS (m/z): 240 (M+)

EXAMPLE 19

Spiro[11-oxo-5,6-dihydropyrido[3,4-b]benzocycloheptene(11H),4'-(2'-methyloxetane)][Compound (II-18)]

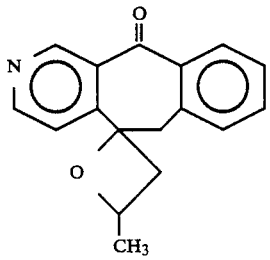

In 3000 ml of dry THF was dissolved 120 g (0.732 mol) of N-isopropylisonicotinamide (1b), and 1000 ml (1.56 mol) of n-butyl lithium was added to the solution at −78° C. in a nitrogen stream, followed by stirring for 2 hours. Then, 70.2 g (0.732 mol) of furfural (10a) was added thereto, followed by stirring at −78° C. for 1 hour. To the reaction mixture was added 1000 ml of water, and the mixture was extracted with 3000 ml of chloroform. The extract was dried over anhydrous sodium sulfate, and the solvent was removed by distillation under reduced pressure to thereby obtain 102 g of 3-[α-hydroxy-(2-furfuryl)]-4-(N-isopropyl)pyridylamide (11a) as a colorless oil.

NMR (CDCl$_3$) δ(ppm): 8.57 (1H, s), 8.52 (1H, d, J=5 Hz), 7.28 (1H, d, J=5 Hz), 7.23 (1H, bs), 5.50–6.70 (3H, m), 3.80–4.30 (1H, m), 1.15 & 1.28 (6H, d, J=6 Hz)

MS (m/z): 260 (M+)

In 1000 ml of methanol was dissolved 102 g of the compound (11a), and 100 ml of a 10N sodium hydroxide aqueous solution was added thereto, followed by stirring at room temperature for 24 hours. The solvent was removed from the reaction mixture by distillation under reduced pressure, and the residue was dissolved in 500 ml of pyridine. To the solution was added 100 ml of acetic anhydride. After stirring at room temperature for 2 hours, the solvent was removed by distillation under reduced pressure. The residue was extracted with 2000 ml of chloroform, the extract was dried over anhydrous sodium sulfate, and the solvent was removed by distillation under reduced pressure. The residue was subjected to silica gel column chromatography using a 1:2 (by volume) mixture of ethyl acetate and n-hexane as an eluent to obtain 42 g (53.3%) of 3-furano-1,3-dihydrofurano[3,4-c]-pyridin-1-one (12a) as a colorless crystal.

NMR (CDCl$_3$) δ(ppm): 8.89 (1H, d, J=5 Hz), 8.86 (1H, d, J=1Hz), 7.81 (1H, dd, J=1 & 5 Hz), 6.56 (1H, s), 6.35–6.46 (2H, m)

MS (m/z): 201 (M+)

In 2000 ml of dry THF was dissolved 60 g (0.299 mol) of the Compound (12a), and 840 ml of allylmagnesium bromide (1.0 mol solution) was added thereto under ice-cooling in a nitrogen stream, followed by stirring at room temperature for 2 hours. To the reaction mixture was added 1000 ml of water, followed by extraction with 3000 ml of chloroform. The extract was dried over anhydrous sodium sulfate, and the solvent was removed by distillation under reduced pressure. The residue was subjected to silica gel column chromatography using a 1:3 (by volume) mixture of ethyl acetate and n-hexane as an eluent to obtain 18 g (21.2%) of α-furano-4-(4-hydroxyhepta-1,6-dien-4-yl)pyridinemethanol (13a) as a colorless oil.

NMR (CDCl$_3$) δ(ppm): 8.52 (1H, s), 8.27 (1H, d, J=6 Hz), 7.91 (1H, s), 7.12 (1H, d, J=6 Hz), 6.58 (1H, s), 6.20–6.40 (2H, m), 4.80–6.10 (6H, m), 2.26–3.00 (4H, m)

MS (m/z): 385 (M+)

Ten grams (35 mmol) of the compound (13a) were dissolved in 100 ml of dimethylformide, and 5.3 g (35 mmol) of t-butyldimethylsilyl chloride and 2.88 g (35 mmol) of imidazole were added thereto in a nitrogen stream, followed by stirring at room temperature for 10 hours. To the mixture was added 100 ml of water, and the mixture was extracted with 500 ml of toluene. The extract was washed with water and dried over anhydrous sodium sulfate. The solvent was removed by distillation under reduced pressure. The residue was purified by silica gel column chromatography using a 1:9 (by volume) mixture of ethyl acetate and n-hexane as an eluent to obtain 13.5 g (96%) of 3-(α-furano-60-t-butyldimethylsilyloxymethyl)-4-(4-hydroxyhepta-1,6-dien-4-yl)pyridine (14a) as a colorless oil.

NMR (CDCl$_3$) δ(ppm): 8.98 (1H, s), 8.36 (1H, d, J=6 Hz), 7.20 (1H, d, J=2 Hz), 6.95 (1H, d, J=6 Hz), 6.75 (1H, s), 6.17 (1H, dd, J=2 & 4 Hz), 5.86 (1H, d, J=4 Hz), 4.78–5.77 (6H, m), 2.15–2.86 (4H, m), 0.84 (9H, s), 0.00 (consistent with tetramethylsilane, s)

MS (m/z): 500 (M+)

In 850 ml of o-dichlorobenzene was dissolved 17 g (42.6 mmol) of the compound (14a), and the solution was heat-refluxed at 195° C. for 4 hours under a nitrogen stream. The solvent was removed from the reaction mixture by distillation, and the residue was subjected to silica gel column chromatography using a 1:3 (by volume) mixture of ethyl acetate and n-hexane as an eluent to obtain 11.0 g (64.7%) of 11-t-butyldimethylsilyloxy-5-hydroxy-5-(2-propen-1-yl)-8,10a-epoxy-11H-5,6,6a,7,8,10a-hexahydropyrido[3,4-b]benzocycloheptene (15a).

NMR (CDCl$_3$) δ(ppm): 8.92 (1H, s), 8.44 (1H, d, J=5 Hz), 7.62 (1H, d, J=5 Hz), 4.75–6.40 (7H, m), 2.48 (2H, d, J=7 Hz), 0.94 (9H, s), 0.09 & 0.11 (6H, s)

MS (m/z): 499 (M+)

Ten grams (25 mmol) of the compound (15a) were dissolved in 300 ml of THF, and 25 ml (1 mol solution) of tetra-n-butylammonium fluoride was added thereto. After stirring at room temperature for 5 hours, 200 ml of water was added thereto, and the mixture was extracted with 500 ml of chloroform. The extract was dried over anhydrous sodium sulfate and distilled under reduced pressure to remove the solvent. The resulting residue was purified by silica gel column chromatography using a 1:2 (by volume) mixture of ethyl acetate and n-hexane as an eluent to obtain 7.0 g (98%) of 5,11-dihydroxy-5-(2-propen-1-yl)-8,10a,epoxy-11H-5,6,6a,7,8,-10a-hexahydro[3,4-b]benzocycloheptene (16a) as a colorless crystal.

NMR (CDCl$_3$) δ(ppm): 8.92 (1H, s), 8.48 (1H, d, J=5 Hz), 7.56 (1H, d, J=5 Hz), 4.85–6.48 (7H, m), 2.47 (2H, d, MS (m/z): 385 (M+)

Seven grams (24.6 mmol) of the compound (16a) were dissolved in 35 ml of dimethylformamide, and the solution was diluted with 35 ml of acetone. To the solution was added 35 ml of 4N Jones' reagent, and the mixture was stirred at room temperature for 5 hours. To the reaction mixture were added 100 ml of methanol and excess sodium hydrogencarbonate, followed by stirring for 10 hours. After any inorganic matter was removed by filtration, the filtrate was concentrated under reduced pressure. The residue was extracted with 500 ml of chloroform, and the extract was dried over anhydrous sodium sulfate and distilled under reduced pressure to remove the solvent. The residue was purified by silica gel column chromatography using a 1:2 (by volume) mixture of ethyl acetate and n-hexane as an eluent to obtain 5.3 g (76.3%) of 5-hydroxy-5-(2-propen-1-yl)-8,10a-epoxy-11H-5,6,6a,7,8,10a-hexahydropyrido[3,4-b]benzocyclohepten-11-one (17a) as a colorless crystal.

NMR (CDCl$_3$) δ(ppm): 8.62 & 8.34 (1H, d, J=5 Hz), 8.45 & 8.37 (1H, s), 7.70 & 7.05 (1H, d, J=5 Hz), 6.73 & 6.26 (1H, d, J=6 Hz), 6.22–6.38 (1H, m), 4.75–6.10 (4H, m), 2.41 & 2.77 (2H, d, J=7 Hz), 2.00–2.40 (3H, m), 1.20–1.90 (2H, m)

MS (m/z): 497 (M+)

In 50 ml of acetic acid was dissolved 3.6 g (12.7 mmol) of the compound (17a), and 10 g of a zinc powder was added thereto under ice-cooling, followed by stirring for 3 hours. The zinc powder was separated by filtration, and the filtrate was concentrated under reduced pressure. To the residue was added a saturated sodium hydrogencarbonate aqueous solution, and the solution was extracted with 300 ml of chloroform. The extract was dried over anhydrous sodium sulfate, and the solvent was removed by distillation under reduced pressure. The resulting residue was dissolved in 250 ml of dioxane, and 5.2 g of p-toluenesulfonic acid was added to the solution, followed by refluxing for 1 hour. The solvent was removed by distillation, and a saturated sodium hydrogencarbonate aqueous solution was added to the residue, and the solution was extracted with 500 ml of chloroform. After drying over anhydrous sodium sulfate and removing the solvent by distillation under reduced pressure, the residue was purified by silica gel column chromatography using a 1:2 (by volume) mixture of ethyl acetate and n-hexane as an eluent to obtain 1.5 g (44.8%) of 5-(2-propen-1-yl)-11H-5,6,6a,7-tetrahydropyrido3,4-b]benzocyclohepten-11-one (19a) as a colorless oil.

NMR (CDCl$_3$) δ(ppm): 8.83 (1H, s), 8.68 (1H, d, J=5 Hz), 7.41 (1H, d, J=5 Hz), 7.14 (1H, dd, J=5 & 6 Hz), 6.03–6.24 (2H, m), 5.00–5.66 (3H, m), 1.65–2.90 (7H, m)

MS (m/z): 267 (M+)

In 100 ml of toluene was dissolved 1.5 g (5.7 mmol) of the compound (19a), and 7.8 g of manganese dioxide was added thereto, followed by refluxing for hours while vigorously stirring. After cooling, the manganese dioxide was separated by filtration, and the filtrate was concentrated under reduced pressure. The residue was purified by silica gel column chromatography using a 1:3 (by volume) mixture of ethyl acetate and n-hexane as an eluent to obtain 1.0 g (66.7%) of 5-hydroxy-5-(2-propen-1-yl)-5,6-dihydropyrido[3,4-b]benzocyclohepten-11(1H)-one (20a) as a colorless crystal.

NMR (CDCl$_3$) δ(ppm): 9.09 (1H, s), 8.70 (1H, d, J=6 Hz), 8.06 (1H, dd, J=2 & 8 Hz), 7.63 (1H, d, J=6 Hz), 7.15–7.57 (2H, m), 4.93–5.95 (3H, m), 3.72 (1H, d, J=16 Hz), 3.21 (1H, d, J=16 Hz), 2.48 (2H, d, J=7 Hz)

MS (m/z): 265 (M+)

In 5 ml of acetic acid was dissolved 0.4 g (1.5 mmol) of the compound (20a), and 5 ml of concentrated sulfuric acid was added thereto, followed by heating at 100° C. for 10 hours while stirring. The reaction mixture was neutralized by addition of sodium hydrogencarbonate under ice-cooling, and then extracted with 200 ml of chloroform. The extract was dried over anhydrous sodium sulfate, and the solvent was removed by distillation under reduced pressure. The residue was subjected to silica gel column chromatography, using a 1:3 (by volume) mixture of ethyl acetate and n-hexane as an eluent to obtain 160 mg (40%) of the entitled compound (II-18) as a colorless oil.

NMR (CDCl$_3$) δ(ppm): 9.10 (1H, s), 8.77 (1H, d, J=6 Hz), 7.97 (1H, dd, J=3 & 8 Hz), 7.63 (1H, d, J=6 Hz), 7.30–7.70 (3H, m). 4.85–5.30 (IH. m). 3.32 (1H, dd, J=6 & 15 Hz), 2.91 (1H, dd, J=6 & 15 Hz), 1.94 (2H, s), 1.24 (3H, d, J=6 Hz)

MS (m/z): 256 (M+)

EXAMPLE 20

5-[(E)-1-Propen-1-yl]-pyrido[3,4-b]benzocyclohepten-11(11H)-one [Compound (II-19)]

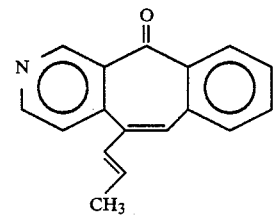

In 40 ml of acetic acid was dissolved 2.6 g (9.8 mmol) of the compound (20a) as obtained in Example 19, and 40 ml of concentrated sulfuric acid was added thereto, followed by heating at 130° C. for 5 hours while stirring. The reaction mixture was neutralized by addition of sodium hydrogencarbonate under ice-cooling and extracted with 2000 ml of chloroform. The extract was dried over anhydrous sodium sulfate, and the solvent was removed by distillation under reduced pressure. The residue was subjected to silica gel column chromatography using a 1:3 (by volume) mixture of ethyl acetate and n-hexane as an eluent to obtain 160 mg (6.2%) of the entitled compound (II-19) as a colorless oil.

NMR (CDCl$_3$) δ(ppm): 9.07 (1H, s), 8.68 (1H, d, J=6 Hz), 7.95 (1H, dd, J=2 & 8 Hz), 7.52 (1H, d, J=6 Hz), 7.30–7.60 (4H, m), 6.44 (1H, d, J=16 Hz), 6.09 (1H, dq, J=6 & 16 Hz), 1.93 (3H, d, J=6 Hz)

MS (m/z): 247 (M+)

EXAMPLE 21

9-Bromo-11-(5-carboxypentylidene)-5,11-dihydropyrido-[4,3-c][1]benzazepin-5(6H)-one [Compound (I-1)]

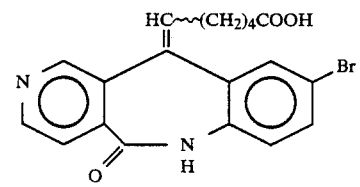

To 7.6 g (16.6 mmol) of 5-carboxypentyltriphenylphosphonium bromide (VIIIa) was added 250 ml of dry THF, and 20.5 ml (32 mmol) of n-butyl lithium was then added thereto under ice-cooling in a nitrogen stream. The resulting mixture was stirred at room temperature for 1 hour. Then, 1.26 g (4.16 mmol) of the compound (II-2) as obtained in Example 2 was added thereto, followed by stirring at room temperature for 2 hours. To the reaction mixture was added 200 ml of water, and the aqueous layer was adjusted to a pH of 4.5 with 4H hydrochloric acid and extracted with 500 ml of chloroform. The extract was dried over anhydrous sodium sulfate, and the solvent was removed by distillation under reduced pressure. The resulting residue was purified by silica gel column chromatography using a 98:2 (by volume) mixture of chloroform and methanol as an eluent to obtain 0.84 g of the entitled compound (I-1) as a colorless Elementary Analysis for $C_{19}H_{17}BrN_2O_3$: Found (%): C 56.81; H 4.38; N 6.94. 8.67 & 8.52 (1H, s), 8.67 & 8.54 (1H, d, J=10 Hz), 7.40-7.81 (3H, m), 7.07 & 7.15 (1H, d, J=9 Hz), 5.99 (1H, t, J=8 Hz), 2.00-2.40 (4H, m), 1.34-1.63 (4H, m)

MS (m/z): 402 (M +2), 400 (M+)

EXAMPLE 22

11-(5-Carboxypentylidene)-7-methyl-5,11-dihydropyrido-[4,3-c][1]benzazepin-5(6H)-one [Compound (I-2)]

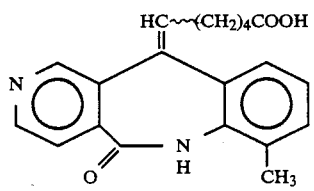

The entitled compound (I-2) was obtained as a colorless oil from the compound (II-6) as prepared in Example 6 and the compound (VIIIa) in the same manner as in Example 21.

Elementary Analysis for $C_{20}H_{20}N_2O_3$: Found (%): C 71.51; H 6.03; N 8.23. Calcd (%): C 71.41; H 5.99; N 8.33.

NMR (DMSO-$d_6$) δ(ppm): 8.65 (1H, bs), 8.55 (1H, bs), 7.71 & 7.65 (1H, d, J=5 Hz), 7.05-7.20 (3H, m), 5.90-5.97 (1H, m), 2.32 & 2.34 (3H, s), 2.05-2.40 (4H, m), 1.35-1.60 (4H, m)

MS (m/z): 336 (M+)

EXAMPLE 23

11-(5-Carboxypentylidene)-9-methoxy-6-methyl-5,11-dihydropyrido-[4,3-c][1]benzazepin-5(6H)-one [Compound (I-3)]

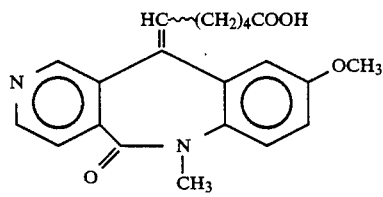

The entitled compound (I-3) was obtained as a colorless oil from the compound (II-5) as obtained in Example 5 and the compound (VIIIa) in the same manner as in Example 21.

Elementary Analysis for $C_{21}H_{22}N_2O_4 \cdot H_2O$: Found (%): C 65.59; H 6.33; N 7.05. Calcd. (%): C 65.61; H 6.29; N 7.29.

NMR (CDCl$_3$) δ(ppm): 8.58 (1H, d, J=5 Hz), 8.51 & 8.48 (1H, s), 7.73 & 7.78 (1H, d, J=5 Hz), 7.12 & 7.19 (1H, d, J=9 Hz), 6.81 & 6.84 (1H, dd, J=3 & 9 Hz), 6.68 & 6.74 (1H, d, J=3 Hz), 5.92 & 5.97 (1H, t J=8 Hz), 3.79 & 3.81 (3H, s), 3.54 (3H, s), 2.21-2.39 (4H, m), 1.53-1.68 (4H, m)

MS (m/z): 366 (M+)

EXAMPLE 24

11-(4-Carboxybutylidene)-5,11-dihydropyrido[4,3-c][1]-benzazepin-5(6H)-one [Compound (I-4)]

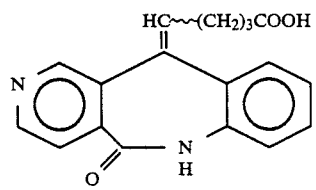

The entitled compound (I-4) was obtained as a colorless oil from the compound (II-1) as prepared in Example 1 and 4-carboxybutyltriphenylphosphonium bromide (VIIIb) in the same manner as in Example 21.

Elementary Analysis for $C_{18}H_{16}N_2O_3 \cdot 0.2H_2O$: Found (%): C 69.31 H 5.26; N 8.87. Calcd. (%), C 69.31 H 5.30; N 8.98.

NMR (DMSO-$d_6$) δ(ppm): 8.65 & 8.66 (1H, d, J=5 Hz), 8.52 & 8.58 (1H, s), 7.67 & 7.73 (1H, d, J=5 Hz), 7.10-7.32 (4H, m), 5.91 & 5.95 (1H, t, J=7 Hz), 2.05-2.40 (4H, m), 1.55-1.83 (4H, m)

MS (m/z): 308 (M+)

EXAMPLE 25

11-(7-Carboxyheptylidene)-5,11-dihydropyrido[4,3-c][1]-benzazepin-5(6H)-one [Compound (I-5)]

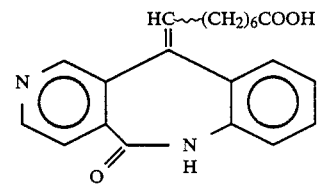

The entitled compound (I-5) was obtained as a colorless oil from the compound (II-1) as prepared in Example 1 and 7-carboxyheptyltriphenylphosphonium bromide (VIIIc) in the same manner as in Example 21.

Elementary Analysis for $C_{21}H_{22}No_2O_3 \cdot 1.3H_2O$: Found (%): C 67.45; H 6.48; N 7.38. Calcd. (%): C 67.47; H 6.63; N 7.49.

NMR (DMSO-$d_6$) δ(ppm): 8.66 (1H, d, J=5 Hz), 8.52 & 8.56 (1H, s), 7.67 & 7.73 (1H, d, J=5 Hz), 7.10-7.31 (4H, m), 5.90 (1H, t, J=8.5 Hz), 2.05-2.29 (4H, m), 1.12-1.44 (8H, m)

MS (m/z): 350 (M+)

EXAMPLE 26

11-(5-Carboxypentylidene)-5-thiomethyl-11(H)-pyrido[4,3-c][1]benzazpin [Compound (I-6)]

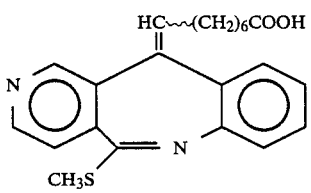

The entitled compound (I-6) was obtained as a colorless oil from the compound (II-10) as prepared in Example 11 and the compound (VIIIa) in the same manner as in Example 21.

Elementary Analysis for $C_{20}H_{20}N_2O_2S$: Found (%): C 67.81; H 5.60; N 7.89. Calcd. (%): C 68.16; H 5.72; N 7.95.

NMR (CDCl$_3$) δ(ppm): 8.59 & 8.60 (1H, d, J=5 Hz), 8.50 & 8.54 (1H, s), 7.59 & 7.66 (1H, d, J=5 Hz), 7.13–7.33 (4H, m), 5.80 & 5.83 (1H, t, J=7 Hz), 2.55 (3H, s), 2.14–2.33 (4H, m), 1.47–1.68 (4H, m)

MS (m/z): 352 (M+)

EXAMPLE 27

(Z)-11-(5-Carboxypentylidene)-5-[(E)-1-propen-1-yl]-(H)-pyrido[3,4-b]benzcycloheptene [Compound (I-7)]

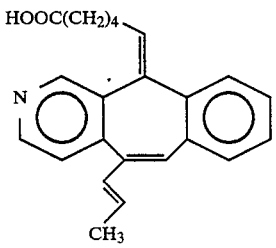

The entitled compound (I-7) was obtained as a colorless oil from the compound (II-18) as synthesized in Example 19 or the compound (II-19) as synthesized in Example 20, and the compound (VIII a) in the same manner as in Example 21.

Elementary Analysis for $C_{21}H_{23}NO_2 \cdot 0.3CH_3COOC_2H_5$: Found (%): C 77.15; H 7.06; N 3.44 Calcd. Calcd. (%): C 76.65; H 7.36; N 4.03.

NMR (CDCl$_3$) δ(ppm): 8.45 (2H, bs), 7.25–7.50 (5H, m), 7.01 (1H, s), 6.39 (1H, d, J=15 Hz), 5.98 (1H, dq, J=6.6 & 15 Hz), 5.72 (1H, t, J=7.7 Hz), 2.05–2.40 (4H, m), 1.88 (3H, dd, J=1.5 & 6.6 Hz), 1.35–1.75 (4H, m)

MS (m/z): 345 (M+)

EXAMPLE 28

11-Ethoxycarbonylmethylene-5,11-dihydropyrido[4,3-c][1]benzazepin-5(6H)-one [Compound (I-8)]

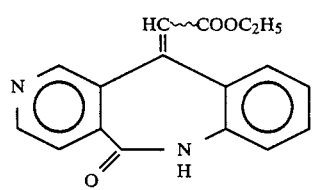

In the same manner as in Example 21, the entitled compound (I-8) was obtained in yield of 3.0 g (64%) from 3.6 g (16.1 mmol) of the compound (II-1) as obtained in Example 1 and 14.4 g (64.3 mmol) of triethyl phosphonoacetate (IXa).

NMR (CDCl$_3$) δ (ppm): 8.73 & 8.64 (1H, d, J=5 Hz), 8.67 & 8.65 (1H, s) 84 (1H, d, J=5 Hz), 7.50–7.05 (4H, m), 6.19 & 6.18 (1H, s), 4.11 & 4.09 (2H, q, J=7 Hz), 1.17 & 1.12 (3H, t, J=7 Hz)

MS (m/z): 294 (M+)

EXAMPLE 29

11-Carboxynethylene-5,11-dihydropyrido[4,3-c][1]benzazaepin-5(6H)-one [Compound (I-9)]

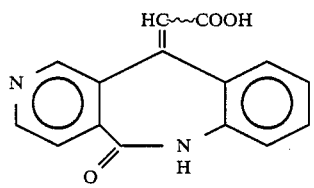

Three grams of the compound (I-8) as obtained in Example 28 were dissolved in 100 ml of methanol, and 20 ml of a 5N sodium hydroxide aqueous solution was added thereto. After stirring at room temperature for 4 hours, the solvent was removed by distillation under reduced pressure, and the residue was extracted with chloroform. The extract was dried over anhydrous sodium sulfate, and the solvent was removed by distillation. The residue was purified by silica gel column chromatography using a 98:2 (by volume) mixture of chloroform and methanol as an eluent to obtain 2.4 g (88.6%) of the entitled compound (I-9) as a colorless crystal.

NMR (DMSO-d$_6$) δ (ppm): 8.65 & 8.58 (1H, s), 8.51 & 8.58 (1H, d, J=5 Hz), 7.62 & 7.66 (1H, d, J=5 Hz), 7.00–7.50 (4H, m), 6.16 & 6.24 (1H, s)

MS (m/z): 266 (M+)

EXAMPLE 30

(E)-11-(5-Carboxypentylidene)-5,11-dihydropyrido[4,3-c][1]benzazepin-5(6H)-one [Compound (I-10E)] and (Z)-11-(5-carboxypentylidene)-5,11-dihydropyrido[4,3-c][1]benzazepin-5(6H)-one [Compound (I-10Z)]

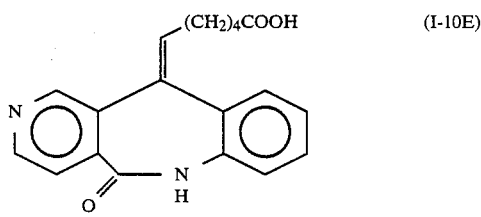 (I-10E)

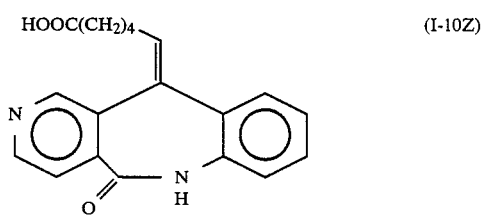 (I-10Z)

A compound (I-10) was obtained from the compound (II-1) as synthesized in Example 1 and the compound (VIIIa) in the same manner as in Example 21.

The compound (I-10) was dissolved in isopropanol, and p-toluenesulfonic acid was added thereto, followed by heat-refluxing for 10 hours to effect esterification After cooling, the solvent was removed by distillation under reduced pressure A saturated sodium hydrocarboncarbonate aqueous solution was added to the residue, and the mixture was extracted with chloroform. The extract was dried over anhydrous sodium sulfate, and the solvent was removed by distillation under reduced pressure. The residue was purified by silica gel column chromatography using ethyl acetate as an eluent to obtain (E)- and (Z)-11-(5-isopropoxycarbonylpentylidene)-5,11-dihydropyrido[4,3-c][1]benzoazepin-5(6H)-one.

Each of the resulting products was hydrolyzed in the same manner as described in Example 29 to obtain the corresponding entitled compound (I-10E) and (I-10Z), respectively, as a colorless crystal.

Compound (I-10E):

Elementary Analysis: $C_{19}H_{18}N_2O_3 \cdot 0.1H_2O$: Found (%): C 70.00; H 5.64; N 8.65. Calcd. (%): C 70.40; H 5.66; N 8.64.

NMR (DMSO-$d_6$) δ (ppm): 8.65 (1H, d, J=6 Hz), 8.56 (1H, s), 7.67 (1H, d, J=6 Hz), 7.10–7.37 (4H, m), 5.95 (1H, t, J=8 Hz), 2.05–2.36 (4H, m), 1.35–1.57 (4H, m)

MS (m/z): 322 (M+)

Compound (I-10Z):

Elementary Analysis for $C_{19}H_{18}N_2O_3 \cdot 3H_2O$: Found (%): C 69.62; H 5.72; N 8.35. Calcd. (%): C 69.50; H 5.72; N 8.55.

NMR (DMSO-$d_6$) δ (ppm): 8.67 (1H, d, J=5 Hz), 8.52 (1H, s), 7.73 (1H, d, J=5 Hz), 7.11–7.32 (4H, m), 5.91 (1H, t, J=6.8 Hz), 1.95–2.37 (4H, m), 1.36–1.58 (4H, m)

MS (m/z): 322 (M+)

EXAMPLE 31

(E)-6-Benzyl-11-(5-carboxypentylidene)-5,11-dihydropyrido[4,3-c][1]benzazepin-5(6H)-one [Compound (I-11E)] and (Z)-6-benzyl-11-(5-carboxypentylidene)-5,11-dihydropyrido[4,3-c][1]benzazepin-5(6H)-one [Compound (I-11Z)]

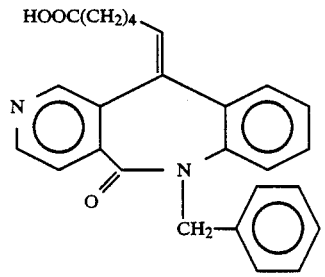
(I-11E)

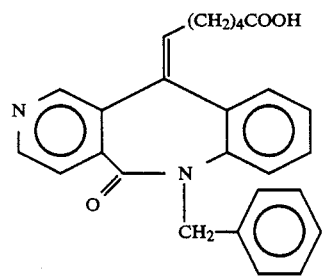
(I-11Z)

The entitled compounds (I-11E) and (I-11Z) were obtained as colorless crystals from the compound (II-7) as synthesized in Example 7 and the compound (VIIIa) in the same manner as in Example 30.

Compound (I-11E):

Elementary Analysis for $C_{26}H_{24}H_2O_3$: Found (%): C 75.60; H 5.75; N 6.81. Calcd. (%): C 75.71; H 5.86; N 6.79.

NMR (CDCl$_3$) δ (ppm): 8.59 (1H, d, J=5 Hz), 8.48 (1H, s), 7.80 (1H, d, J=5 Hz), 7.09–7.29 (9H, m), 5.86 (1H, t, J=7 Hz), 5.49 (1H, d, J=15 Hz), 5.08 (1H, d, J=15 Hz), 2.15–2.38 (4H, m), 1.38–1.71 (4H, m)

MS (m/z): 412 (M+)

Compound (I-11Z):

Elementary Analysis for $C_{26}H_{24}N_2O_3 \cdot 1.3H_2O$: Found (%): C 71.62; H 5.86; N 6.34. Calcd. (%): C 71.64; H 6.15; N 6.43.

NMR (CDCl$_3$+DMSO-$d_6$) δ (ppm): 8.60 (1H, bs), 8.50 (1H, bs), 7.74 (1H, d, J=5 Hz), 7.10–7.35 (4H, m), 5.92 (1H, t, J=7.5 Hz), 5.66 (1H, d, J=15 Hz), 4.98 (1H, d, J=15 Hz), 1.98–2.35 (4H, m), 1.40–1.72 (4H, m)

MS (m/z): 412 (M+)

EXAMPLE 32

(E)-11-(5-Carboxypentylidene)-6-methyl-5,11-dihydropyrido[4,3-c][1]benzazepin-5(6H)-one [Compound (I-12E)] and (Z)-11-(5-carboxypentylidene)-6-methyl-5,11-dihydropyrido[4,3-c][1]benzazepin-5(6H)-one [Compound (I-12Z)]

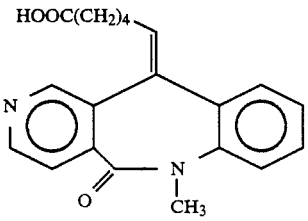
(I-12E)

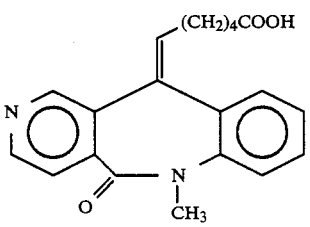
(I-12Z)

The entitled compounds (I-12E) and (I-12Z) were obtained as colorless crystals from the compound (II-8) as synthesized in Example 9 and the compound (VIIIa) in the same manner as in Example 30.

Compound (I-12E):

Elementary Analysis for $C_{20}H_{20}N_2O_3 \cdot 0.6H_2O$: Found (%): C 69.00; H 6.22; N 7.81. Calcd. (%): C 69.19; H 6.15; N 8.07.

NMR (CDCl$_3$) δ (ppm): 9.07 (1H, s), 8.62 (1H, d, J=5 Hz), 7.12–7.34 (4H, m), 7.08 (1H, d, J=5 Hz), 5.92 (1H, t, J=7 Hz), 3.58 (3H, s), 2.15–2.40 (4H, m), 1.48–1.75 (4H, m)

MS (m/z): 336 (M+)

Compound (I-12Z):

Elementary Analysis for $C_{20}H_{20}N_2O_3$: Found (%): C 71.35; H 5.96; N 8.21. Calcd. (%): C 71.41; H 5.99; N 8.33.

NMR (CDCl$_3$) δ (ppm): 9.02 (1H, s), 8.60 (1H, d, J=5 Hz), 7.10–7.37 (5H, m), 5.94 (1H, t, J=8 Hz), 3.57 (3H, s), 2.20–2.38 (4H, m), 1.40–1.70 (4H, m)

MS (m/z): 336 (M+)

EXAMPLE 33

(E)-11-(5-Carboxypentylidene)-6-methoxy-11H-pyrido[4,3-c][2]benzazepin [Compound (I-13E)] and (Z)-11-(5-carboxypentylidene)-6-methoxy-11H-pyrido[4,3-c][2]benzazepin [Compound (I-13Z)

(I-13E)

(I-13Z)

In the same manner as in Example 30, 11-(5-isopropoxycarbonylpentylidene)-6,11-dihydropyrido[4,3-c][2]-benzazepin-6(5H)-one was prepared from the compound (II-11) obtained in Example 12 and the compound (VIIIa).

Eight grams (22 mmol) of the resulting compound were dissolved in 800 ml of chloroform, and 200 ml of pyridine and 25 ml of phosphorus oxychloride were added to the solution. After stirring at room temperature for 2 hours, the solvent was removed by distillation under reduced pressure, and to the residue was added 400 ml of methanol, followed by stirring at 50° C. for 3 hours. The solvent was removed by distillation under reduced pressure, and to the residue was added a saturated aqueous solution of excess sodium hydrogencarbonate. The mixture was extracted with 2000 ml of chloroform, and the extract was dried over anhydrous sodium sulfate. The solvent was removed therefrom by distillation, and the residue was subjected to silica gel column chromatography using a 1:4 (by volume) mixture of ethyl acetate and n-hexane as an eluent to obtain (E)- and (Z)-11-(5-isopropoxycarbonylpentylidene)-6-methoxy-11H-pyrido[4,3-c][2]benzazepin.

Each of the products was hydrolyzed in the same manner as in Example 29 to obtain the corresponding (I-13E) and (I-13Z), respectively, as colorless crystals.

Compound (I-13E):

Elementary Analysis for C$_{20}$H$_{20}$N$_2$O$_3$.0.8H$_2$O: Found (%): C 68.53; H 5.93; N 7.83. Calcd. (%): C 68.48; H 6.21; N 7.99.

NMR (CDCl$_3$) δ (ppm): 8.45 (1H, s), 8.37 (1H, d, J=5.5 Hz), 7.73 (1H, dd, J=1 & 7.5 Hz), 7.52 (1H, dt, J=1 & 7.5 Hz), 7.37 (1H, dt, J=1 & 7.5 Hz), 7.24 (1H, d, J=7.5 Hz), 7.11 (1H, d, J=5.5 Hz), 5.81 (1H, t, J=7.5 Hz), 4.02 (3H, s), 2.10–2.40 (4H, m), 1.45–1.75 (4H, m)

MS(m/z): 336 (M+)

Compound (I-13Z):

Elementary Analysis for C$_{20}$H$_{20}$N$_2$O$_3$.0.7H$_2$O: Found (%): C 69.02; H 6.01; N 7.82. Calcd. (%): C 68.83; H 6.18; N 8.03.

NMR (CDC;3) δ (ppm): 8.37 (2H, bs), 7.66 (1H, d, J=7.5 Hz), 7.50 (1H, t, J=7.5 Hz), 7.34 (1H, t, J=7.5 Hz), 7.28 (1H, d, J=7.5 Hz), 7.15 (1H, d, J=5 Hz), 5.84 (1H, t, J=7 5 Hz), 4.01 (3H, s), 2.12–2.40 (4H, m), 1.45–1.75 (4H, m)

MS (m/z): 336 (M+)

EXAMPLE 34

(E)-11-(5-Carboxypentylidene)-6,11-dihydropyrido[4,3-c][2]benzazepin-6(5H)-one [Compound (I-14E)]

In 20 mg of n-propanol was dissolved 200 mg (0.6 mmol) of the compound (I-13E) as obtained in Example 33, and 5 ml of 4N hydrochloric acid was added thereto, followed by stirring at room temperature for 5 hours. The solvent was removed by distillation under reduced pressure, and the residue was extracted with 200 ml of chloroform. The extract was dried over anhydrous sodium sulfate, and the solvent was removed by distillation under reduced pressure. The residue was purified by silica gel column chromatography using a 98:2 (by volume) mixture of chloroform and methanol as an eluent to obtain 65 mg (86%) of the entitled compound (I-14E) as a colorless crystal.

Elementary Analysis for C$_{19}$H$_{18}$N$_2$O$_3$.1.3H$_2$O: Found (%): C 66.00; H 5.73; N 7.85. Calcd. (%): C 66.00; H 6.01; N 8.16.

NMR (DMSO-d$_6$) δ (ppm): 8.37 (1H, s), 8.35 (1H, d, J=5 Hz), 7.86 (1H, dd, J=1 & 7.5 Hz), 7.62 (1H, dt, J=1 & 7.5 Hz), 7.46 (1H, t, J=7.5 Hz), 7.29 (1H, d, J=7.5 Hz), 7.06 (1H, d, J=5 Hz), 5.84 (1H, t, J=7 Hz), 2.05–2.35 (4H, m), 1.35–1.58 (4H, m)

MS (m/z): 322 (M+)

EXAMPLE 35

(Z)-11-(5-Carboxypentylidene)-6,11-dihydropyrido[4,3-c][2]benzazepin-6(5H)-one [Compound (I-14Z)]

The entitled compound (I-14Z) was obtained as a colorless crystal from the compound (I-13Z) obtained in Example 33 in the same manner as in Example 34.

Elementary Analysis for C$_{19}$H$_{18}$N$_2$O$_3$.0.3H$_2$O: Found (%): C 69.75; H 5.78; N 8.22. Calcd (%): C 69.62; H 5.72; N 8.55.

NMR (DMSO-d$_6$) δ (ppm): 8.38 (1H, d, J=5 Hz), 8.32 (1H, s), 7.81 (1H, dd, J=1.5 & 8 Hz), 7.61 (1H, dt, J=1.5 & 8 Hz), 7.44 (1H, dt, J=1.5 & 8 Hz), 7.34 (1H, d, J=8 Hz), 7.15 (1H, d, J=5 Hz), 5.94 (1H, t, J=7 Hz), 2.00–2.31 (4H, m), 1.35–1.58 (4H, m)

MS (m/z): 322 (M+)

EXAMPLE 36

11-(5-Carboxypentylidene)-11H-5,6-dihydropyrido[4,3-c][1]benzazepin [Compound (I-15)]

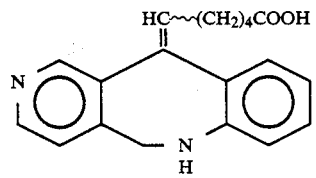

In 50 ml of ethanol was dissolved 0.55 g (1.6 mmol) of the compound (I-6) obtained in Example 26, and 120 mg of 10% Palladium-on-carbon was added thereto, followed by stirring at 60° C. for 6 hours in a hydrogen stream. The catalyst was separated by filtration, and the filtrate was concentrated under reduced pressure. The residue was purified by silica gel column chromatography using a 98:2 (by volume) mixture of chloroform and methanol as an eluent to obtain 350 mg (72.8%) of the entitled compound (I-15) as a colorless Elementary Analysis for $C_{19}H_{20}N_2O_2$: Found (%): C 74.01; H 6.54; N 9.03. Calcd. (%): C 74.00; H 6.54; N 9.08.

NMR (CDCl$_3$) δ (ppm): 8.51 (1H, d, J=5 Hz), 8.41 (1H, s), 7.21 (1H, dd, J=1 & 7 Hz), 7.19 (1H, d, J=5 Hz), 7.02 (1H, dt, J=1 & 7 Hz), 6.73 (1H, t, J=7 Hz), 6.44 (1H, d, J=7 Hz), 6.02 (1H, t, J=7.5 Hz), 4.80 (1H, bs), 3.88 (1H, bs), 2.00–2.40 (4H, m), 1.45–1.75 (4H, m)

MS (m/z): 308 (M+)

EXAMPLE 37

11-Carboxymethylene-5-thiomethyl-11H-pyrido[4,3-c][1][2]benzazepin [Compound (I-16)]

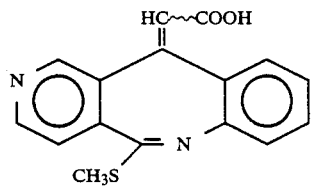

The entitled compound (I-16) was obtained a a colorless crystal from the compound (I-10) prepared in Example 11 and triethyl phosphonoacetate (IXa) in the same manner as in Examples 28 and 29.

Elementary Analysis for $C_{16}H_{12}N_2O_2S \cdot 0.4H_2O$: Found (%): C 63.32; H 3.94; N 8.93. Calcd. (%): C 63.32; H 4.25; N 9.23.

NMR (DMSO-d$_6$) δ (ppm): 8.68 & 8.76 (1H, d, J=5 Hz), 8.60 & 8.67 (1H, s), 7.69 & 7.70 (1H, d, J=5 Hz), 7.12–7.45 (4H, m), 6.15 & 6.20 (1H, s), 2.56 & 2.57 (3H, s)

MS(m/z): 296 (M+)

EXAMPLE 38

5-Carboxymethylene-5,11-dihydropyrido(3,4-c)[1]benzazepin-11(10H)-one [Compound (I-17)]

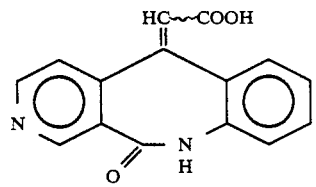

The entitled compound (I-17) was obtained as a colorless crystal from the compound (II-13) obtained in Example 14 and the compound (VIIId) in the same manner as in Example 37.

Elementary Analysis for $C_{15}H_{10}N_2O_3$: Found (%): C 67.53; H 3.78; N 10.39. Calcd. (%): C 67.66; H 3.79; N 10.52.

NMR (DMSO-d$_6$) δ (ppm): 8.84 & 8.87 (1H, s), 8.54 & 8.68 (1H, d, J=5 Hz), 7.39 & 7.41 (1H, d, J=5 Hz), 6.85–7.38 (4H, m), 6.15 & 6.26 (1H, s)

MS (m/z): 266 (M+)

EXAMPLE 39

5-(5-Carboxypentylidene)-11-thiomethyl-5H-pyrido[3,4-c][1]benzazepin [Compound (I-18)]

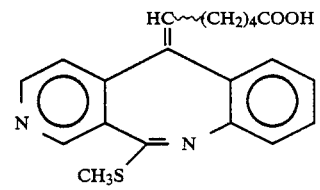

The entitled compound (I-18) was obtained as a colorless oil from the compound (II-15) obtained in Example 16 and the compound (VIIIa) in the same manner as in Example 21.

Elementary Analysis for $C_{20}H_{20}N_2O_2S \cdot 0.2H_2O$: Found (%): C 67.45; H 6.09; N 7.69. Calcd. (%): C 67.47; H 5.78; N 7.87.

NMR (CDCl$_3$) δ (ppm): 8.96 & 9.03 (1H, s), 8.64 & 8.66 (1H, d, J=5 Hz), 7.06–7.32 (5H, m), 5.77–5.79 (1H, t, J=6.5 Hz), 2.57 (3H, s), 2.15–2.38 (4H, m), 1.40–1.72 (4H, m)

MS(m/z): 352 (M+)

EXAMPLE 40

(E)-5-(5-Carboxypentylidene)-5,11-dihydropyrido[3,4-c][1]benzazepin-11(10H)-one [Compound (I-19E)] and (Z)-5-(5-carboxypentylidene)-5,11-dihydropyrido[3,4-c][1]benzazepin-11(10H)-one [Compound (I-19Z)]

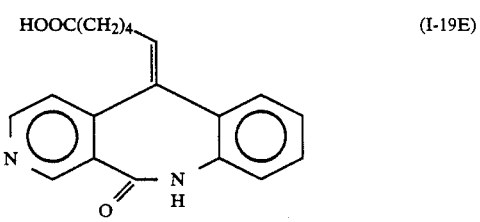

(I-19E)

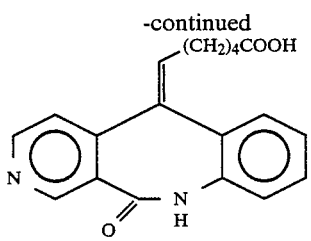

(I-19Z)

The entitled compounds (I-19E) and (I-19Z) were obtained as colorless crystals from the compound (II-13) prepared in Example 14 and the compound (VIIIa) in the same manner as in Example 30.

Compound (I-19E):

Elementary Analysis for $C_{19}H_{18}N_2O_3$: Found (%): C 70.75; H 5.61; N 8.68. Calcd. (%): C 70.79; H 5.63; N 8.69.

NMR (DMSO-$d_6$) δ (ppm): 8.94 (1H, s), 8.71 (1H, d, J=5 Hz), 7.11–7.33 (5H, m), 5.88 (1H, t, J=7 Hz), 2.02–2.38 (4H, m), 1.38–1.59 (4H, m)

MS (m/z): 322 (M+)

Compound (I-19Z):

Elementary Analysis for $C_{19}H_{18}N_2O_3$: Found (%): C 70.53; H 5.59; N 8.57. Calcd. (%): C 70.79; H 5.63; N 8.69.

NMR (DMSO-$d_6$) δ (ppm): 8.87 (1H, s), 8.70 (1H, d, J=5 Hz), 7.12–7.37 (5H, m), 5.98 (1H, t, J=8 Hz), 2.02–2.34 (4H, m), 1.35–1.58 (4H, m)

MS (m/z): 322 (M+)

EXAMPLE 41

(E)-5-(5-Carboxypentylidene)-10-methyl-5,11-dihydropyrido[3,4-c][1]benzazepin-11(10H)-one [Compound (I-20E)] and
(Z)-5-(5-carboxypentylidene)-10-methyl-5,11-dihydropyrido[3,4-c][1]benzazepin-11(10H)-one [Compound (I-20Z)]

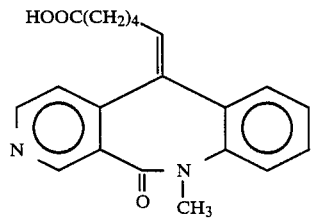

(I-20E)

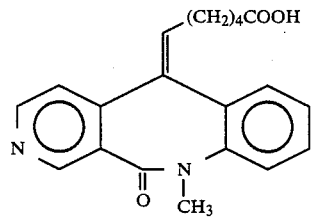

(I-20Z)

The entitled compounds (I-20E) and (I-20Z) were obtained as colorless crystals from the compound (II-14) obtained in Example 15 and the compound (VIIIa) in the same manner as in Example 30.

Compound (I-20E):

Elementary Analysis for $C_{20}H_{20}N_2O_3.0.6H_2O$: Found (%): C 69.00; H 6.22; N 7.81. Calcd. (%): C 69.19; H 6.15; N 8.07.

NMR (CDCl$_3$) δ (ppm): 9.08 (1H, s), 8.62 (1H, d, J=5 Hz), 7.12–7.34 (4H, m), 7.08 (1H, d, J=5 Hz), 5.92 (1H, t, J=7 Hz), 3.58 (3H, s), 2.15–2.38 (4H, m), 1.48–1.75 (4H, m)

MS (m/z): 336 (M+)

Compound (I-20Z):

Elementary Analysis for $C_{20}H_{20}N_2O_3.0.28CHCl_3$: Found (%): C 65.97; H 5.69; N 7.56. Calcd. (%): C 65.86; H 5.53; N 7.57.

NMR (CDCl$_3$) δ (ppm): 9.02 (1H, s), 8.60 (1H, d, J=5 Hz), 7.10–7.38 (5H, m), 5.94 (1H, t, J=8 Hz), 3.57 (3H, s), 2.23–2.38 (4H, m), 1.45–1.70 (4H, m)

MS (m/z): 336 (M+)

EXAMPLE 42

5-(5-Carboxypentyl)-5,11-dihydropyrido[3,4-c][1]benzazepin-11(10H)-one [Compound (I-21)]

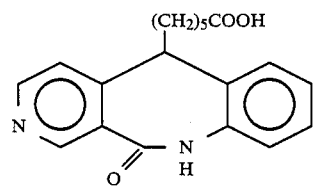

One gram (3.1 mmol) of 5-(5-carboxypentylidene)-5,11-dihydropyrido[3,4-c][1]benzazepin-11(10H)-one [Compound (I-19)] as obtained in Example 40 was dissolved in 80 ml of ethanol, and 1.5 g of platinum dioxide was added thereto. The mixture was stirred at room temperature for 3 hours in a hydrogen stream. The catalyst was removed by filtration, and the filtrate was concentrated under reduced pressure. The resulting residue was subjected to silica gel column chromatography using a 98:2 (by volume) mixture of chloroform and methanol as an eluent to obtain 0.35 g (35%) of the entitled compound (I-21) as a colorless oil.

Elementary Analysis for $C_{20}H_{22}N_2O_3.0.5H_2O$: Found (%): C 68.34; H 6.10; N 8.39. Calcd. (%): C 68.45; H 6.35; N 8.40.

NMR (DMSO-$d_6$) δ (ppm): 8.86 (1H, s), 8.62 (1H, d, J=5 Hz), 7.41 (1H, d, J=5 Hz), 7.05–7.38 (4H, m), 4.00 (1H, t, J=8 Hz), 0.95–2.35 (10H, m)

MS (m/z): 324 (M+)

EXAMPLE 43

5-(5-Carboxypentylidene)-11-thiomethyl-5H-10,11-dihydropyrido[3,4-c][1]benzazepin [Compound (I-22)] and
5-(5-carboxypentylidene)-5H-10,11-dihydropyrido[3,4-c][1]benzazepin [Compound(I-23)]

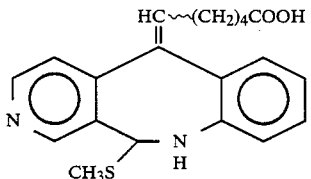

(I-22)

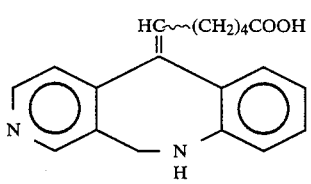

(I-23)

In 50 ml of ethanol was dissolved 300 mg (0.85 mmol) of the compound (I-18) as obtained in Example 39, and 6 g of 10% palladium-on-carbon was added thereto. The mixture was stirred at room temperature for 5 hours in a hydrogen stream. The catalyst was separated by filtration, and the filtrate was concentrated under reduced pressure. The resulting residue was purified by silica gel column chromatography using a 98:2 (by volume) mixture of chloroform and methanol as an eluent to obtain 70 mg (23%) of the entitled compound (I-22) and 60 mg of the compound (I-23) both as a colorless oil.

Compound (I-22):

Elementary Analysis for $C_{20}H_{22}N_2O_2S$: Found (%): C 67.68; H 6.12; N 7.83. Calcd. (%): C 67.77; H 6.26; N 7.90.

NMR (CDCl$_3$) δ (ppm): 8.50 (1H, d, J=5 Hz), 8.48 (1H, s), 7.05-7.35 (3H, m), 6.91 (1H, t, J=8 Hz), 6.86 (1H, t, J=8 Hz), 5.98 (1H, t, J=7.5 Hz), 2.99 (3H, s), 2.05-2.38 (4H, m), 1.45-1.75 (4H, m)

MS (m/z): 354 (M+)

Compound (I-23):

Elementary Analysis for $C_{19}H_{20}N_2O_2$: Found (%): C 73.73; H 6.46; N 8.98. Calcd. (%): C 74.00; H 6.54; N 9.08.

NMR (CDCl$_3$) δ (ppm): 8.42 (1H, d, J=5 Hz), 8.32 (1H, s), 7.05-7.35 (3H, m), 6.74 (1H, t, J=8 Hz), 6.71 (1H, d, J=8 Hz), 6.41 (2H, bs), 5.77 (1H, t, J=7.5 Hz), 2.15-2.38 (4H, m), 1.45-1.75 (4H, m)

MS (m/z): 308 (M+)

EXAMPLE 44

Tablets having the following composition were prepared in a usual manner.

Compound (I-12E): 200 mg
Lactose: 60 mg
Potato starch: 30 mg
Polyvinyl alcohol: 2 mg
Magnesium stearate: 1 mg
Tar pigment: trace

EXAMPLE 45

Powders having the following composition were prepared in a usual manner.

Compound (I-13E): 200 mg
Lactose: 270 mg

EXAMPLE 46

A syrup having the following composition was prepared in a usual manner.

Compound (I-6): 200 mg
Purified sugar: 40 g
Ethyl p-hydroxybenzoate: 40 mg
Propyl p-hydroxybenzoate: 10 mg
Strawberry flavor: 0.1 cc
Water to make: 100 cc While the invention has been described in detail and with reference to specific embodiments thereof, it will be apparent to one skilled in the art that various changes and modifications can be made therein without departing from the spirit and scope thereof.

What is claimed is:

1. A pyridine derivative represented by formula (I):

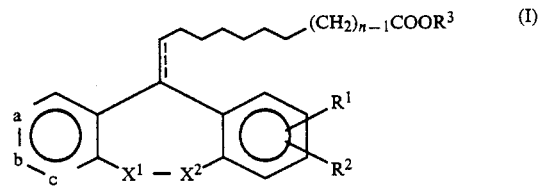

wherein ═ represents a single bond or a double bond; $R^1$ and $R^2$, which may be the same or different, each represents a hydrogen atom, a lower alkyl group, a hydroxy group, a lower alkoxy group, a lower alkylthio group, or a halogen atom, or when taken together form a methylenedioxy group; $R^3$ represents a hydrogen atom or a lower alkyl group; n represents an integer of from 1 to 10; $X^1$—$X^2$ represents

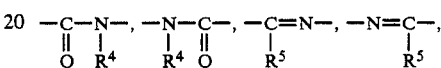

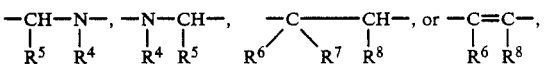

wherein $R^4$ represents a hydrogen atom, a lower alkyl group, an unsubstituted aralkyl group having from 7 to 13 carbon atoms or an aralkyl group having from 7 to 13 carbon atoms substituted with a lower alkyl group, a lower alkoxy group, a lower alkenyl group, a trifluoromethyl group, a halogen atom or a methylenedioxy group; $R^5$ represents a hydrogen atom, a lower alkoxy group, or a lower alkylthio group; and $R^6$ and $R^8$, which may be the same or different, each represents a hydrogen atom, a lower alkyl group, or a lower alkenyl group; $R^7$ represents a hydrogen atom; or $R^6$ and $R^7$ when taken together form

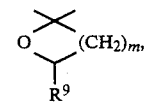

wherein $R^9$ represents a lower alkyl group, and m represents an integer of from 1 to 3; and any one of a, b, and c represents a nitrogen atom or an N-oxide (N→O), with the other two representing a carbon atom, or a pharmaceutically acceptable salt thereof.

2. The pyridine derivative of claim 1, in which a is N or b is N and $X^1$—$X^2$ represents

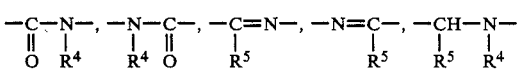

or 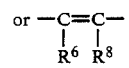

wherein $R^4$ represents a hydrogen atom, a lower alkyl group, or an unsubstituted aralkyl group; $R^5$ represents a hydrogen atom, a lower alkoxy group, or a lower alkylthio group; and $R^6$ and $R^8$, which may be the same or different, each represents a hydrogen atom, a lower alkyl group, or a lower alkenyl group.

3. The pyridine derivative of claim 2, in which a is N and b and c are both C.

4. The pyridine derivative of claim 2, in which b is N and a and c are both C.

5. The pyridine derivative of claim 2, in which n is 1 to 7.

6. The pyridine derivative of claim 1, in which one of $R^1$ and $R^2$ is hydrogen, $C_{1-6}$ alkyl, $C_{1-4}$ alkoxy, halogen and the other is hydrogen.

7. A pharmaceutical composition comprising a thromboxane $A_2$ synthase-inhibiting amount of a compound of claim 1, together with a pharmaceutically acceptable carrier or diluent.

8. A pharmaceutical composition comprising, as the active ingredients, a thromboxane $A_2$ synthase-inhibiting amount of a compound of claim 1 together with another pharmacologically active ingredient and a pharmaceutically acceptable carrier or diluent.

9. The pharmaceutical composition of claim 7, in unit dosage containing from 0.01 to 1000 mg of the compound of claim 1.

* * * * *

UNITED STATES PATENT AND TRADEMARK OFFICE
CERTIFICATE OF CORRECTION

PATENT NO. : 4,971,964
DATED : November 20, 1990
INVENTOR(S) : SUZUKI, Koji et al It is certified that error appears in the above-identified patent and that said Letters Patent is hereby corrected as shown below:

Column 12, lines 40-50, please correct the formula to include double bonds as follows:

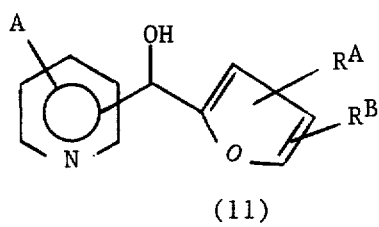

(11)

Column 16, line 64, change "c$^l$" to read --c$^1$--.

Column 31, line 63, before "ml" insert --200--.

Column 39, line 52, before "hours" insert --6--.

UNITED STATES PATENT AND TRADEMARK OFFICE
CERTIFICATE OF CORRECTION

PATENT NO. : 4,971,964

DATED : November 20, 1990

INVENTOR(S) : SUZUKI, Koji et al.

It is certified that error appears in the above-identified patent and that said Letters Patent is hereby corrected as shown below:

Column 48, line 24, change "mg" to read --ml-- (both occurrences).

Signed and Sealed this

Eighth Day of September, 1992

Attest:

DOUGLAS B. COMER

*Attesting Officer*  *Acting Commissioner of Patents and Trademarks*